US007170052B2

(12) United States Patent
Furutani et al.

(10) Patent No.: US 7,170,052 B2
(45) Date of Patent: Jan. 30, 2007

(54) MALDI-IM-ORTHO-TOF MASS SPECTROMETRY WITH SIMULTANEOUS POSITIVE AND NEGATIVE MODE DETECTION

(75) Inventors: Hiroshi Furutani, La Jolla, CA (US); Michael V. Ugarov, Houston, TX (US); Kimberly Prather, Encinitas, CA (US); J. Albert Schultz, Houston, TX (US)

(73) Assignees: Ionwerks, Inc., Houston, TX (US); The Regents of the University of California, Oakland, CA (US)

( * ) Notice: Subject to any disclaimer, the term of this patent is extended or adjusted under 35 U.S.C. 154(b) by 179 days.

(21) Appl. No.: 11/025,640

(22) Filed: Dec. 29, 2004

(65) Prior Publication Data

US 2005/0230615 A1 Oct. 20, 2005

Related U.S. Application Data

(60) Provisional application No. 60/533,936, filed on Dec. 31, 2003.

(51) Int. Cl.
*H01J 49/00* (2006.01)
*B01D 59/44* (2006.01)

(52) U.S. Cl. ...................... 250/287; 250/281; 250/282; 250/286; 250/288

(58) Field of Classification Search ................. 250/281
See application file for complete search history.

(56) References Cited

U.S. PATENT DOCUMENTS

| | | | | |
|---|---|---|---|---|
| 6,140,639 | A * | 10/2000 | Gusev et al. | 250/288 |
| 6,639,213 | B2 * | 10/2003 | Gillig et al. | 250/286 |
| 6,683,299 | B2 * | 1/2004 | Fuhrer et al. | 250/287 |
| 6,797,945 | B2 * | 9/2004 | Berggren et al. | 250/288 |
| 6,806,465 | B2 * | 10/2004 | Anderson et al. | 250/287 |
| 6,897,437 | B2 * | 5/2005 | Fuhrer et al. | 250/287 |
| 6,989,528 | B2 * | 1/2006 | Schultz et al. | 250/281 |
| 2001/0032929 | A1 * | 10/2001 | Fuhrer et al. | 250/281 |
| 2002/0158196 | A1 * | 10/2002 | Berggren et al. | 250/288 |
| 2004/0094705 | A1 * | 5/2004 | Wood et al. | 250/288 |
| 2004/0113064 | A1 * | 6/2004 | Fuhrer et al. | 250/287 |
| 2005/0035284 | A1 * | 2/2005 | Schultz et al. | 250/287 |
| 2005/0230615 | A1 * | 10/2005 | Furutani et al. | 250/287 |
| 2006/0138317 | A1 * | 6/2006 | Schultz et al. | 250/287 |

OTHER PUBLICATIONS

He, L. and Myrray, K.K, "337 nm Matrix-assisted Laser Desorption/Ionization of Single Aerosol Particles", J. Mass Spectrometry 34 (1999) 909-914.*

Gillig, et al., "Coupling High-Pressure MALDI with Ion Mobility/Orthogonal Time-of-Flight Mass Spectrometry"; Anal. Chem. pp. 72, 3965, (2000).

Huang, et al., "Polyfunctional Fullerene Derivatives as UV-MALDI Matrices to Detect Peptides and Proteins", J. Fullerene Sci. Technol. 7, 541 (1999).

(Continued)

*Primary Examiner*—Nikita Wells
*Assistant Examiner*—Bernard Souw
(74) *Attorney, Agent, or Firm*—Fulbright & Jaworski LLP

(57) ABSTRACT

An ion mobility/mass spectrometry method and instrument using aerosolized samples and dual positive and negative mode detection is described. Sample preparation methods are also described.

55 Claims, 13 Drawing Sheets

OTHER PUBLICATIONS

Hybl et al., “Laser-Induced Breakdown Spectroscopy Detection and Classification of Biological Aerosols”; Appl. Spectrosc. 57, v10, p. 1207 (2003).

Karas, et al., “Matrix-Assisted Ultraviolet laser Desorption of Non-Volatile Compounds”, Int. J. Mass Spectrom. Ion Processes 1987, 78, (53).

Schurenberg et al., “Laser Desorption/Ionization Mass Spectrometry of Peptides and Proteins with Particle Suspension Matrixes”; Anal. Chem. 1999, 71 (221-229).

Shiea et al., “Use of a Water-Soluble Fullerene Derivative as Precipitating Reagent and Matrix-Assisted Laser Desorption/Ionization atrix to Selectively Detect Charged Species in Aqueous Solutions”, Anal. Chem. 75, 3587 (2003).

Tanaka, et al., “Protein and polymer Aanlyses up to m/z 100000 by Laser Ionization Time-of-flight Mass Spectrometry”; Rapid Commun. Mass Spectrom. 88, 2, (151).

Woods, et al., “A study of Peptide-Peptide Interactions Using MALDI Ion Mobility o-TOF and ESI Mass Spectrometry”; J. Amer. Soc. Mass Spectr. 2002, 13, (166-169).

* cited by examiner

MALDI from Aerosolilzed Fullerene and Dynorphin 1-8

Pos & Neg Mass Spectra from a Single Dynorphin Particle (#191)

A

- 110 Generate aerosol nanoparticulates
- 115 Charge the nanoparticulates
- 66 Select the nanoparticulates using an aerodynamic lens
- 120 Accelerate the charged nanoparticulates
- 125 Select and inject the charged nanoparticulates

B

- 110 Generate aerosol nanoparticulates
- 115 Charge the nanoparticulates
- 118 Select the nanoparticulates using a differential ion mobility spectrometer
- 120 Accelerate the charged nanoparticulates
- 125 Select and inject the charged nanoparticulates

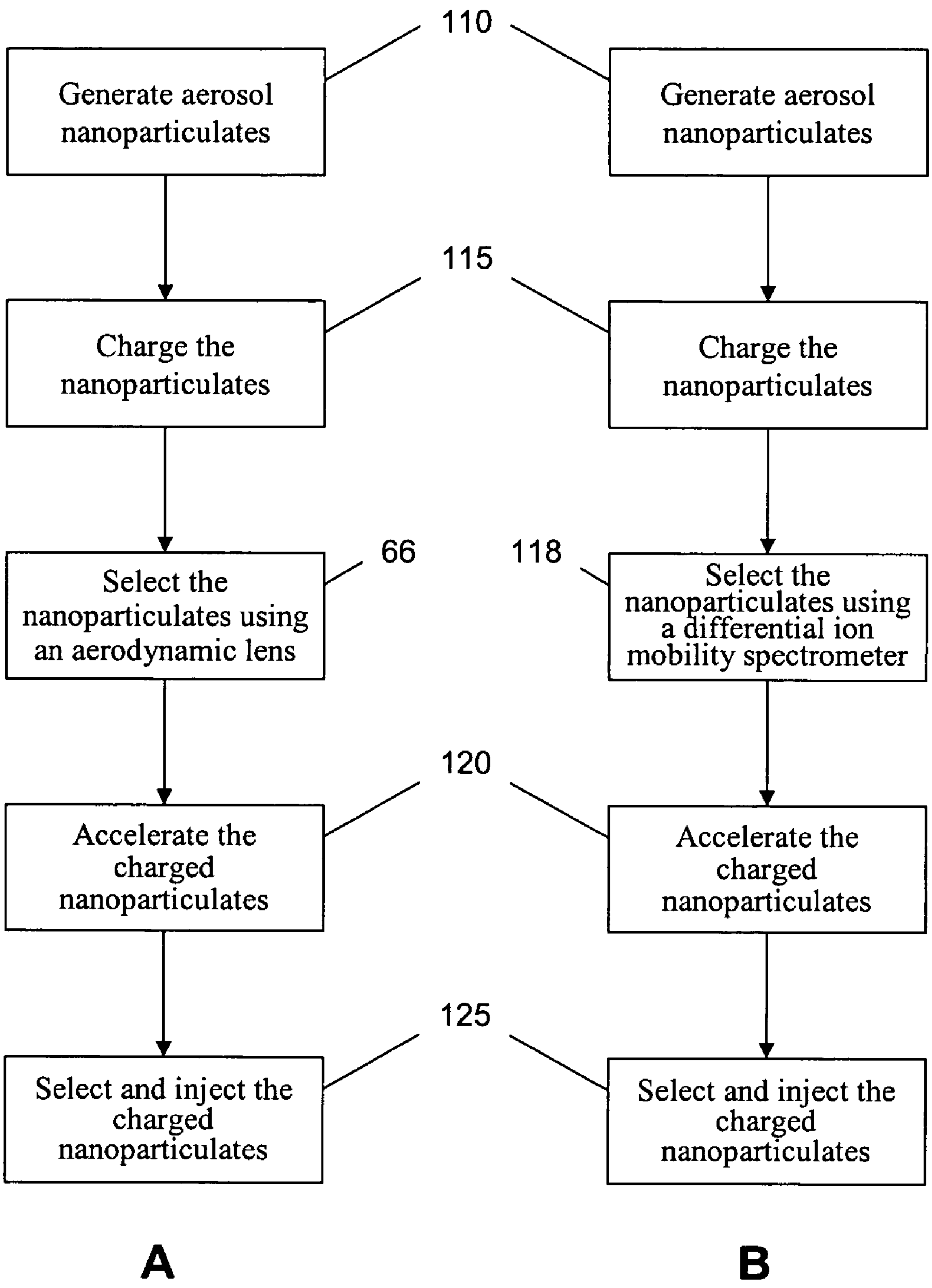

FIG. 13

MALDI-IM-ORTHO-TOF MASS SPECTROMETRY WITH SIMULTANEOUS POSITIVE AND NEGATIVE MODE DETECTION

This application claims priority to U.S. application Ser. No. 60/533,936, filed on Dec. 31, 2003.

This invention was made, in part, with U.S. government support. The U.S. government may have some rights in the invention.

TECHNICAL FIELD

The present invention relates generally to instrumentation for the characterization and analysis of elemental and molecular ions from aerosolized particles based at least on their structures and mass-to-charge ratios as gas-phase ions using an improved spectrometer and an optional use of MALDI ionization matrix and combining this matrix with a dual Ion Mobility-orthogonal time of flight mass spectrometer having simultaneous positive and negative mode detection. More specifically, to such instrumentation which provides for rapid and sensitive analysis of composition, sequence, and/or structural information relating to organic molecules, including biomolecules, and inorganic constituents from airborne particulates with size ranging from a few tens of nanometers to several tens of microns. The invention further relates to methods for depositing an aerosolized mixture of particles onto or into a solid surface from which subsequent laser or energetic particle desorption can be performed.

BACKGROUND OF THE INVENTION

MALDI (Matrix-Assisted Laser Desorption Ionization; a laser desorption technique)-mass spectrometry of biomolecular ions was first demonstrated in parallel efforts by Tanaka et al. using small metal particles suspended in glycerol and by Karas and Hillenkamp (*Int. J. Mass Spectrom. Ion Processes* 1987, 78, (53)) and by Tanaka (*Rapid Commun. Mass Spectrom.* 88, 2, (151)) using small organic acid molecules as matrices. In using either the particle matrices or the small organic acid matrices the matrix performs the dual function of both absorbing the laser light and ionizing the non-light absorbing analyte biomolecules through specific and poorly understood chemical reactions. The particle matrices actually perform yet a third function by physisorbing the analyte from solution onto the particle surface. The organic acid matrices met with greater success in the marketplace in part due to their ease of use over wider applicable mass ranges for proteins and peptides. However, they are not completely free of defects, the most notable being the narrow band optical absorption of the excitation radiation, and the non-uniform distributed analyte during the co-crystallization of matrix and analyte.

Efforts to use the slurried small particles as matrices has languished in all but a few laboratories primarily because of the fundamental problem that the adsorbed protein must also be surrounded by just the right amount of glycerol (interestingly, while other organics have been used in place of glycerol, none appear to work nearly as well). The drying process to establish the correct amount of glycerol is dynamic under vacuum so that the “right amount” is only transitorily achieved. This leaves just a few minutes at a specific time and place near the edge of the sample droplet for acquisition of good spectra. Nevertheless the small metal particulates, because of their flat optical absorbance over a large range of wavelengths, have a huge potential advantage over organic matrices because in principle a wider variety of lasers can be used to perform the experiments. Shurenberg (*Anal. Chem.* 1999, 71; pp. 221–229) has reviewed the literature and performed a number of illuminating experiments, all of which establish the current understanding of these nanoparticulate matrices. In summary, for protein masses of up to around 13 kDa, the particle/glycerol system will give identical spectra as organic acid matrices (though with about an order of magnitude less sensitivity). Above this mass range the slurried particles cannot compete with the performance of chemical matrices. Any refractory particle seems to work—including carbon nanosoot and titanium nitride—as long as the particle size is significantly below 1 micron and as long as glycerol is added.

Although the MALDI technique has greatly enhanced the art of mass spectrometric analysis of biomolecules, there remains much room for improvement. It would be desirable to develop a particle based MALDI matrix that eliminates the need for glycerol addition and the concomitant problems associated with it. The ideal particle matrix would include an efficient, broadband absorber to allow one to take advantage of electromagnetic radiation sources covering a wide range of wavelengths, especially laser sources operating at wavelengths other than 337 nm from a nitrogen laser. Work by Hillenkamp and others has used pulsed infrared lasers for MALDI analysis of analytes such as peptides and oligonucleotides codeposited with water. The water acts both as matrix and proton donor and absorbs the pulsed IR laser radiation to allow time of flight mass spectrometry of the desorbed analyte. An efficient particle matrix absorber would also allow one to use low laser power excitation over a wide, nonspecific spectral range. Beyond the intrinsic wide band optical absorbance of many solids, the size of the particulates can be tailored to increase optical absorbance in certain wavelength ranges so that the matrix absorbance can be tailored to a specifically desirable excitation wavelength. The efficient particle matrix would also permit the use of smaller molar ratio of matrix/analyte, by orders of magnitude, than is possible now with small organic matrices. It would be useful to employ such a matrix in a mass spectrometric method having a chromatographic preseparation based for example on molecular shape selectivity (IMS) or based on liquid chromatography to separate isobaric matrix interference from the mass spectrum of the analyte. Finally, the ability to efficiently combine matrices with analyte to form small aerosols which can be directly ablated after introduction into a mass spectrometer has real advantages which include among others more heterogeneous distribution of analyte within the matrix and elimination of substrate effects upon the ionization process.

BRIEF SUMMARY OF THE INVENTION

The present invention is directed to a system and method for the matrix-assisted laser desorption ionization ion mobility and mass spectrometric analysis of elemental and molecular ion species. The following more readily describes the present invention.

In one aspect of the present invention, there is a method of preparing a sample for analysis by laser desorption mass spectrometry, comprising the steps of: combining the sample with a matrix comprising a native or derivatized fullerene; and, producing aerosol particles from the combined sample and matrix. In some embodiments, the native or derivatized fullerene is selected from the group consisting of $C_{60}$, $C_{70}$, $C_{76}$, $C_{84}$, and combinations thereof. In some embodiments, the surface derivatized inorganic particle used as said matrix is selected from the group consisting of titanium nitride, aluminum nitride, boron nitride, carbonitride, carbon boron nitride, gold, molybdenum, copper, copper lithium alloy, platinum, silver, and combinations thereof. In some embodiments, the sample comprises peptides or proteins, or combinations thereof. In some embodiments, the peptides or protein may be antibodies, enzymes or combinations thereof. In some embodiments, the sample comprises a nucleic acid, a nucleic acid base, a nucleotide, a nucleoside, or combinations thereof. In some embodiments, the sample comprises lipids, lipoproteins, or combinations thereof. In some embodiments, the sample comprises phospholipids, ceramides, derivatives thereof, or combinations thereof. In some embodiments, the sample comprises glycosylated proteins, glycosylated lipids, lipopolysaccharides, glycans, or combinations thereof. In some embodiments, the sample comprises natural or synthetic organic polymers, natural or synthetic inorganic polymers, or combinations thereof. In some embodiments, the sample comprises small organic molecules, organometallic molecules, or combinations thereof.

In some embodiments, there is a method of preparing a sample for analysis by laser desorption mass spectrometry, comprising the steps of: combining the sample with a matrix comprising a native or derivatized nanotube; and, producing aerosol particles from the combined sample and matrix. In some embodiments, the nanotube is a derivatized nanotube. In some embodiments, the native or derivatized nanotube is a native or derivatized single wall nanotube. In some embodiments, the sample comprises peptides, proteins, antibodies, enzymes, or combinations thereof. In some embodiments, the sample comprises a nucleic acid, a nucleic acid base, a nucleotide, a nucleoside, or combinations thereof. In some embodiments, the sample comprises a lipoprotein. In some embodiments, the sample comprises phospholipids, ceramides, derivatives thereof, or combinations thereof. In some embodiments, the sample may comprise glycosylated proteins, glycosylated lipids, lipopolysaccharides, glycans, or combinations thereof. In some embodiments, the sample comprises natural or synthetic organic polymers, natural or synthetic inorganic polymers, or combinations thereof. In some embodiments, the sample comprises small organic molecules, organometallic molecules, or combinations thereof. There is also a method of preparing a sample for analysis by laser desorption mass spectrometry, comprising the steps of: combining the sample with a matrix comprising a surface derivatized inorganic particle; and, producing aerosol particles from the combined sample and matrix. There is also a method of preparing a sample for analysis by laser desorption mass spectrometry, comprising the steps of: combining the sample with a matrix comprising nanoparticulates; and, producing aerosol particles from the combined sample and matrix.

In some embodiments, there is a method for the analysis of samples using ion mobility resolved mass spectrometric data comprising the steps of: introducing a sample comprising a liquid droplet or aerosol into a desorption source; ionizing and desorbing gaseous analyte species from said liquid droplet or aerosol; separating said analyte species from one another in an ion mobility cell; and, resolving said analyte species in an orthogonal time-of-flight mass spectrometer. In some embodiments, the method further comprises the step of forming said liquid droplet or aerosol with a vibrating orifice aerosol generator. In some embodiments, the vibrating orifice aerosol generator generates droplets at the rate of up to 10 MHz. In some embodiments, the step of ionizing and desorbing comprises ionizing and desorbing with coaxial laser irradiation. In some embodiments, the sample is an aerosolized sample of a previously airborne pathogen. In some embodiments, the pathogen is a bacteria, virus, prion, or cell. In some embodiments, the sample is an aerosolized sample from a distribution of whole cells or whole cell lysate. In some embodiments, the method further comprises the step of correlating said ion mobility resolved mass spectrometric data with fluorescence data. In some embodiments, the step of ionizing and desorbing comprises multiply impinging said sample with an energy source. In some embodiments, the energy source is selected from the group consisting of a laser, a pulsed X-ray source, a chopped continuous infrared source, and a pulsed electron beam source.

In another embodiment of the present invention, there is an instrument for the collection of ion mobility resolved mass spectrometric data comprising: an aerosol formation apparatus to form an aerosol; a desorption ionization source coupled to said apparatus and capable of desorbing and ionizing species comprising the aerosol; two ion mobility cells fluidly coupled to said aerosol formation apparatus, each mobility cell comprising a drift tube having a separation axis configured 180° to the separation axis of the drift tube of the other mobility cell; and, at least one time-of-flight mass spectrometer fluidly coupled to said mobility cell and having a flight tube orthogonal to the axis of the drift tube of the mobility cell. In some embodiments, one of the mobility cells operates in positive mode and the other mobility cell operates in negative mode. In some embodiments, the desorption ionization source comprises a laser. In some embodiments, the laser emits a radiation beam which is coaxial to the path of a particle or droplet of the aerosol. In some embodiments, the laser emits a radiation beam which is coaxial to a particle or droplet train of said aerosol. In some embodiments, the aerosol comprises a sample in a fullerene-based matrix. In some embodiments, the aerosol comprises a sample in a nanotube-based matrix. In some embodiments, the nanotubes are single wall nanotubes. In some embodiments, aerosolized matrix particles formed from said aerosol are fluidly coupled to the mobility cell using a single particle injection apparatus. In some embodiments, the single particle injection apparatus is a converging nozzle aerosol interface. In some embodiments, the instrument further comprises a differentially pumped vacuum stage. In some embodiments, the aerosol formation apparatus is a vibrating orifice aerosol generator. In some embodiments, the vibrating orifice aerosol generator couples said mobility cells and said time-of-flight mass spectrometer to a liquid chromatograph. In some embodiments, the vibrating orifice aerosol generator is directly interfaced to said mobility cell. In some embodiments, the desorption ionization source comprises a laser. In some embodiments, the laser emits a radiation beam which is coaxial to then path of a particle or droplet of said aerosol. In some embodiments, the laser emits a radiation beam which is coaxial to a particle or droplet train of said aerosol. In some embodiments, the mobility cell further comprises multiapertures and periodic focusing fields. In some embodiments, the instrument further comprises a pathogen detection device which correlates the ion mobility resolved mass spectrometric data with fluorescence data. In some embodiments, the instrument further comprises a heated substrate fluidly coupled to or located within at least one of the ion mobility cells. The heated substrate may comprise molybdenum or tantalum or other appropriate materials.

In one aspect of the present invention, there is an apparatus for generating matrix particles for implantation into a sample for desorption/ionization comprising: a nanoparticle source; a charging device fluidly coupled to and receiving nanoparticles from said nanoparticle source and forming charged nanoparticles; a focusing lens fluidly coupled to the charging device to focus said charged nanoparticles, a particle accelerator fluidly coupled to said focusing lens; and, a sample stage to position a sample and receive charged nanoparticles from said particle accelerator.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 13 shows an instrumental scheme for generating matrix particles, charging them and injecting them into a viscous liquid or a solid surface

DETAILED DESCRIPTION OF THE INVENTION

Figure 1:
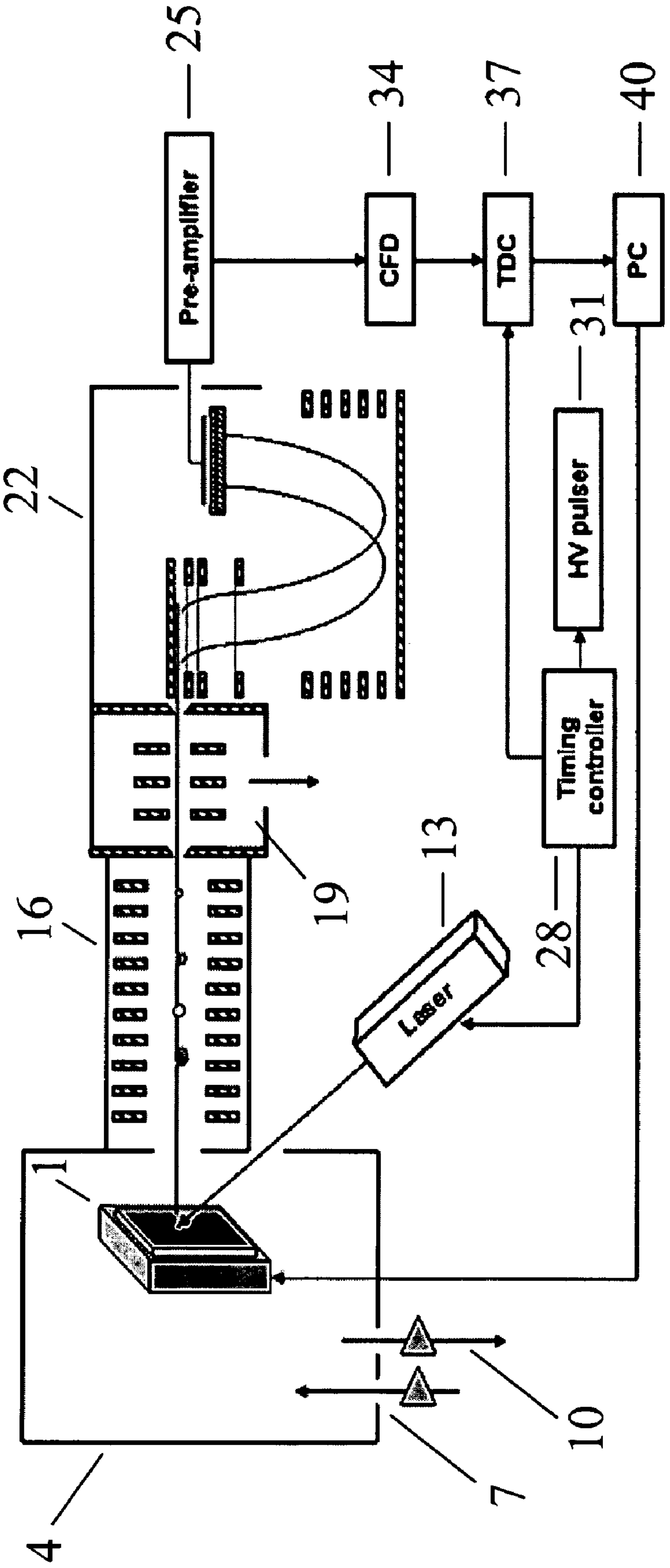
FIG. 1 is a schematic illustration of the MALDI—Ion Mobility/Orthogonal Time-of-Flight mass spectrometer.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," and "comprising" are interchangeable and one of skill in the art is cognizant that these terms are open ended terms.

As used herein, ATOFMS is defined as a single particle aerosol time of flight mass spectrometer.

As used herein, ES is an abbreviation for and is defined as electrospray and refers to an electrospray ion source. ESI is an abbreviation for electrospray ionization.

As used herein, IMS is an abbreviation for and is defined as ion mobility spectrometry. The abbreviation IM is defined as ion mobility and refers to an ion mobility cell, especially when it is used in conjunction with other analytical instrumentation such as mass spectrometry.

As used herein, MALDI/IM/o-TOF is an abbreviation for and defined as a matrix assisted laser desorption ionization/ion mobility/orthogonal time-of-flight mass spectrometer.

As used herein, IM/o-TOF is an abbreviation for and defined as an ion mobility/orthogonal time-of-flight mass spectrometer.

Dual IM/oTOF is an abbreviation for the instrument (shown in FIG. 8) comprising a mobility tube assembly in which the production of ions is performed in a middle region of the ion mobility cell after which positive and negative ions are separated in different directions into respective oTOF spectrometers.

As used herein, MALDI is an abbreviation for and is defined as matrix assisted laser desorption ionization.

As used herein, MS is an abbreviation for and is defined as mass spectrometry.

As used herein, "nanoparticle" is a particle having dimensions ranging from about 0.2 nanometers to about 100 nanometers. The terms "nanoparticle" and "nanoparticulate" are used interchangeably herein.

As used herein, SIMS is an abbreviation for and is defined as secondary ion mass spectrometry.

As used herein, TOF is an abbreviation for "time-of-flight" and is defined as a time-of-flight mass spectrometer.

As used herein, "o-TOF" or "oTOF" is a time-of-flight mass spectrometer having a flight tube arranged orthogonally to the separation axis of a preceding separation technique.

As used herein, VOAG is defined as a vibrating orifice aerosol generator.

In copending U.S. application Ser. No. 10/861,970 (filed Jun. 4, 2004), specially derivatized fullerene nanoparticulates acting as sensitive MALDI matrices for peptides and lipids and the use of IMS for separation of matrix interferences were disclosed. U.S. application Ser. No. 10/861,970 is expressly incorporated by reference as though fully described herein. In copending U.S. application Ser. No.

10/861,962 (filed Jun. 4, 2004), the implantation of gold particles for improved MALDI matrices for biological samples was disclosed. U.S. application Ser. No. 10/861,962 is expressly incorporated by reference as though fully described herein. In copending U.S. applications Ser. No. 10/969,643 (filed Oct. 20, 2004) and Ser. No. 10/967,715 (filed Oct. 18, 2004), a new mobility cell design incorporating alternating regions of high and low electric field is disclosed. U.S. application Ser. Nos. 10/969,643 and 10/967,715 are expressly incorporated by reference as though fully described herein. This represented an improvement in the MALDI matrix by obviating the need to use conventional MALDI acid matrices and the problems associated therewith. However, despite these advances, further improvements in sample preparation and instrumental efficiency would be helpful.

In the present invention, aerosolized particles may be either from environmentally sampled airborne particulates with sizes ranging down to a few nanometers or they may also be from specially prepared particles containing matrix and analyte which are ionized after introduction into the mobility/mass spectrometer. Thus as used herein, the production or formation of aerosol particles encompasses the aerosolization of samples by aerosolization techniques known in the art and by the sampling of already-formed aerosols, such as, but not limited to, airborne atmospheric samples. A procedure is described by which the solution phase intermixing of any particulate matrix with analyte is followed by localizing both analyte and matrix into an aerosolized droplet of a few micron diameter (which can, if desired, ultimately be dried to create a particle whose dimensions can be precisely created over a diameter ranging from a few nanometers up to several microns). This preparation scheme forces intimate mixing of particles and analyte which may otherwise segregate (because of different solubilities) during evaporation of solvent. Thus the single particle ionization of such a specially prepared aerosolized solution droplet (or solid particle created by drying the droplet) is coupled with MALDI-Ion Mobility-orthogonal time of flight mass spectrometry (MALDI-IM-oTOF) to provide a solution to longstanding and vexing problems associated with MALDI sample preparations using the "dried droplet" technique in which a solution (or suspension) of matrix and analyte is deposited onto a surface and allowed to slowly dry. The segregation of matrix and analyte into separate crystals and into macroscopic regions on the sample surface after drying is a well known and undesirable phenomena and is more often the rule than the exception when employing the dried droplet preparation method for MALDI. By contrast the aerosolized matrix preparation gives more quantitatively useful signal intensities either when ablated as single solution droplet or dried particulates or when analyzed after impacting either the solution droplets or dried particulates onto a surface to form a thin coating of the aerosol particles containing matrix and analyte. Furthermore, for the first time, simultaneous acquisition of positive and negative MALDI spectra can be acquired as the single aerosol particulates are introduced into either a dual single particle mass spectrometer or into a specially designed gas filled ion mobility cell in which the particulates can be ablated and ionized, followed by ion mobility separation of negative and positive ions into separate mass spectrometers. Thus the simultaneous acquisition of positive and negative correlated mass spectra or correlated positive and negative IM-MS spectra from the same sample droplet preparation allows unique particle by particle correlations which may increase structural assignment accuracy in on-line MALDI analysis. This is also useful in providing correlations which may help in establishing disease state biomarker ions or in determining the presence of environmentally transported pollutant or biohazards to name just two practical examples. Additionally, this sample production and instrumental approach are both ideally suited to allow two-step ionizations in which the aerosol is first impinged with an energy source to desorb analyte on (or from within) the aerosol particle followed by a second localized pulsed energy source to ionize the desorbed neutral analyte. Introduction of the particle into the mobility cell also allows adequate time for multiple desorption/ionization (single, double, etc.) pulsed sequences so that information on the depth distribution of analyte within a singe aerosol particlulate could be profiled for the first time.

In copending U.S. application Ser. No. 10/861,970, it was shown that specially derivatized fullerene nanoparticulates act as sensitive MALDI matrices for peptides and lipids. The fullerenes may be any of the native or derivatized $C_{60}$, $C_{76}$, or $C_{84}$ species or any native or derivatized higher fullerene. The fullerenes may also include related compounds such as nanotubes, including single walled nanotubes. These nanotubes may or may not be derivatized with a chemical moiety. All of the other applications discussed in the context of conventional fullerene and related compounds would be equally applicable here. In addition to the fullerene-based matrices, matrices of inorganic particles such as titanium nitride, aluminum nitride, boron nitride, carbonitride and carbon boron nitride as well as finely divided metal clusters including gold, molybdenum, copper, copper lithium alloy, platinum, and silver. Although the bulk of the disclosure focuses on the specific embodiments of fullerene and inorganic particles as matrix particulates, it should be understood that other particulates are also within the scope of the present invention.

The MALDI-IM-oTOF (matrix assisted laser desorption/ionization-ion mobility-orthogonal time of flight mass spectrometry) technique (See *Anal. Chem.* 72, 3965 (2000)) has now been used to analyze and separate bio-ions from the ionized nanoparticulate fullerenes. Derivatization of the fullerenes has demonstrated that these particulates can be used as matrices. In particular, $(NHC(CH_2OH)_3)_n$, $(C_4H_9SO_3Na)_n$ (see *J. Fullerene Sci. Technol.* 7, 541 (1999) and $((CH_2)_4SO_3)_6$ (see *Anal. Chem.* 75, 3587 (2003)) clusters have been used. However, other derivatives may be used and are within the scope of the present invention. It was also shown that the ion mobility can be used to separate such particulate matrices from the bioanalyte (see copending U.S. application Ser. No. 10/861,970 herein incorporated by reference). Gold implantation into biochemical and biological samples using gold nanoparticulates can be used as well (see copending U.S. application Ser. No. 10/861,962 herein incorporated by reference). Presently, fullerene nano-matrices are used as test systems to produce well defined 1.5 micron aerosol particles comprising fullerene matrix and bio-analyte. After production at atmospheric pressure these particles exit a differentially pumped converging nozzle and travel with a carrier gas stream into a nominally 2 Torr expansion region. The particles are focused by gas dynamics and are optically tracked and injected after a short transition region into a specially designed MALDI-dual ion mobility (IM) cell-dual o-TOF where the particles can be sequentially 1) ablated/ionized, 2) separated simultaneously into positive and negative analyte ions which may include biomolecular ions, 3) desorbed ions are sorted by size by ion mobility for each polarity ion stream, and 4) mobility separated ions are mass analyzed in two orthogonal time of flight mass spectrometers optimized for each ion polarity. The bio-analytes can be any or a variety of molecular ions or elements, including, but not limited to, biological molecules such as peptides, proteins (such as antibodies, enzymes, prions, inter alia), lipids (such as, for example, phospholipids, ceramides, and derivatives, thereof), nucleic acids, nucleotides, nucleosides, nucleic acid bases (purines, pyrimidines, derivatives thereof, etc. Other examples include oligonucleotides, lipoproteins, glycosylated proteins, glycosylated proteins, glycosylated lipids, lipopolysaccharides, and glycans. Associations of the different biomolecules into structures (e.g. antibody-antigen, molecule-receptor) through non-covalent interactions can also be analyzed in such a spectrometer yielding particularly powerful information about the gas phase conformation of the complex compared to mass spectrometer systems which only measure the mass/charge ratio of such complexes. Molecules other than biomolecules may also be potential analytes, these include, but are not limited to, synthetic organic and inorganic polymers, small organic and organometallic molecules, inorganic molecular ions, and elements.

The most widely used sample preparation method for MALDI analysis is the dried droplet technique whereby a mixed solution of analyte and matrix is deposited onto a sample plate and allowed to dry. During the drying, co-crystallization of the matrix and analyte is seldom achieved and more often the analyte segregates into the grain boundaries between the matrix crystallites. This has relegated MALDI to a semi-quantitative technique. Analyte segregation produces the undesired result that some regions of the droplet surface, when interrogated by a focused laser, produce no analyte signal even when analyte is present. These effects have only been partially mitigated by reducing matrix crystallite size and by moving the laser to average the signal from many areas of the droplet preparation. Furthermore, it is impossible to acquire simultaneous negative and positive MALDI spectra from a surface which is biased to repel either one or the other polarity bio-ions into the mass spectrometer. Also, the mass resolution and sensitivity is limited by the presence of "chemical noise" background and by the spatial roughness and charging effects associated with the droplet preparation. Finally, the presence of cationic adducts from residual salts of sodium and potassium produce contaminant peaks which complicate spectral assignments in a one dimensional mass spectrometer instrument where only the m/z of the ion is measured.

The combination of aerosolized matrix preparation with MALDI-Ion Mobility-orthogonal time of flight mass spectrometry (MALDI-IM-oTOF) solves most of the longstanding and vexing problems associated with MALDI sample preparations and furthermore elevates MALDI to a technique allowing on-line interrogation of solution phase chemistries. Furthermore, for the first time, simultaneous acquisition of positive and negative MALDI spectra from the same sample preparation—and indeed the same aerosol particle—will allow unique particle by particle correlations which may increase structural assignment accuracy in on-line MALDI analysis as well as providing correlations to other techniques (such as laser induced fluorescence) which may, for example, help in establishing disease state biomarker ions or in identifying airborne pathogens. A useful procedure is to derivatize the matrix particle not only with a chemical functionalization which promotes ionization, but also with a specific anchor molecule which will abstract from solution and attach specific analyte molecules to the surface anchor according to chemical type or structure or activity (e.g., DNA or RNA complement, antibody, antigen). Such an engineered particle might be used to harvest specific molecules from a solution using a specific attachment to the anchor followed by centrifugation. The particle might also contain a portion which is magnetic which would then allow concentration of the particle/analyte adduct by a magnetic field. Furthermore the aforementioned functionalized and anchor site-labeled particle could contain specific tags (either of a single type or in combination) such as 1) fluorescence molecules or 2) mass specific adducts such as pure isotopically labeled molecules or 3) minor occurrence elemental isotopes (of some element which is rare in the mixture to be analyzed) which is furthermore immobilized in the matrix particle and would be released from the particle only by the process during which the attached analyte is desorbed into the mass spectrometer. With such a custom designed particle matrix, the detection of the label during the ionization process acts as a cue to when a particular particle containing the anchor is being ablated so that correlations can be made to analytes desorbed after being specifically bound to the particle surface by interaction with the molecularly specific anchor. Thus a system for using mixtures of matrix particles from several groups of differently labeled particle surfaces is useful for simultaneously extracting different types of molecular information from a solution (e.g., saliva, urine, or blood plasma). In contrast, if dried droplet MALDI-MS is employed all the analyte information is scrambled into one very complicated one dimensional mass spectrum which is averaged over many different matrix-analyte combinations which are all likely to be present in the area sampled by the focused laser used in traditional MALDI.

One example of a matrix particle for the present invention is nanoparticles coated with a material such as nanocrystalline diamond. An isotopic labeling of the nanocrystalline diamond thin film is prepared by co-depositing elemental tags using for example certain ratios of silicon isotopes of 28, 29, and 30. A specific DNA complement can be anchored through C—C covalent bonds to the surface of the diamond and this forms an exceptionally stable DNA anchor site which when the particulate is put into solution can be used to adsorb and desorb the matching DNA complement as many as fifty times without degradation. Mixtures of groups of such particles—each group containing a specific anchor label and a specifically artificially prepared ratio of silicon mass 28, 29, and 30—could then be all simultaneously used in solution and then serialized one by one through the dual IM-oTOF for simplification of the analysis of complex solutions. Other such anchored surface structures including, for example, antibodies or antibody antigen assemblies would also be tractable within this approach.

The present invention extends the earlier efforts utilizing fullerenes or implanted gold clusters as novel MALDI matrices. The efficient coupling of 2 Torr dual IM-oTOF and MALDI from standard and nanoparticulate matrix preparations is disclosed.

Although examples will focus on specific fullerene matrix preparations, the instrument and method will be generalized so that any aerosolized preparation can be analyzed. In particular surface engineered gold nanoparticles are useful in this effort. It has recently been shown that massive gold clusters (1 nm diameter $Au_{400}^{4+}$) work exceptionally well as SIMS matrices when implanted into thin films of pure peptides or proteins (*Rapid Commun. Mass Spectrom.*, in press, and that the implanted gold clusters subsequently work well as MALDI matrices (in unpublished work)). These surface-engineered nanogold materials can then be successfully used in an aerosol MALDI dual-IM-oTOF spectrometer. This testing of surface-deposited materials using our existing MALDI-IM-oTOF is another aspect of the present invention. Yet another aspect of the invention is the tracking and single particle ablation of ultrafine environmental aerosols which may or may not be combined with nanoparticulate matrix or may be even coated with more conventional matrices such as paranitroaniline or other well known MALDI matrices followed by ionization and analysis in a dual IM-oTOF. A further significant aspect of our invention is the introduction into a dual ion mobility-orthogonal time of flight mass spectrometer of solution droplets (which may contain matrix) which would allow for rapid interrogation of solution phase reaction kinetics. Another significant application of our invention is the introduction into a dual ion mobility-orthogonal time of flight mass spectrometer of solution droplets which contain specific mixtures of matrix (which may be nanoparticulates or traditional matrices or mixtures of both) and may contain analyte so that on line MALDI may be performed. It is also possible to make these aerosol droplets and either deposit them with or without drying onto a surface (as an alternative to dried droplet preparation) or charge either the droplet or the dried particulate, and accelerate this resulting charged aerosol into a surface such as a biological tissue as a way of implantation of matrix into the very near surface region of the solid or semi-solid material.

In the present invention, we combine a new approach to MALDI matrix preparation and their use for analysis through a technique of aerosolized introduction into either an existing ATOFMS technology or specially modified MALDI-IM-oTOF spectrometer. The ion mobility spectrometer allows for the separation of the co-desorbed analyte from the nanoparticulate cluster matrix such as fullerene clusters.

The biomolecular analytes can form adducts particularly if they are extracted directly from physiological fluid or tissue. In these cases many types of ions can be formed from the intact analyte including radical ions, MH+ or (M–H)− as well as ions from positively or negatively ionized analyte attachments: (alkali cations, such as potassium and sodium, biologically active metals such as iron, copper, magnesium, or intentionally attached metals such as uranium stains, gold, silver, tungsten, platinum all of which can attached to various types of the bioanalyte or synthetic polymer analyte. Many of these elements form adducts with small organics (such as drugs or explosives). In most cases in modern MALDI mass spectrometry the attachment of the adduct is scrupulously avoided since it complicates the one dimensional mass spectrum, often hopelessly so. In contrast, the chromatographic space available with MALDI-IM-oTOF can turn these adducted species into a huge advantage by allowing production of redundant ions which are separated by IMS and provide additional verification of the identity of a parent ion. Ion Mobility Spectrometry (IMS) has been combined with MALDI for analysis of peptides and other large molecules at femtomole loading (*J. Amer. Soc. Mass Spectrom.,* 13, 166–169 (2002).

The instrument shown schematically in FIG. 1 allows separation by IMS (with a resolution of ranging from 35 to 100) on the basis of ion volume (shape) while retaining the inherent sensitivity and mass accuracy of orthogonal time of flight MALDI. Such instruments allow separation by IMS (with a resolution of ranging from about 35 to 100) on the basis of ion volume (shape) while retaining the inherent sensitivity and mass accuracy of orthogonal time of flight MALDI. A sample (1), such as a biological sample, is housed within a MALDI chamber (4) having gas inlet (7) and pumping mechanism (10). A laser (13) irradiates the sample (1) and laser desorbed ions enter mobility cell (16) and are separated by their mobilities. The mobility-separated ions then enter a differential pumping region (19) and then enter a time-of-flight mass spectrometer (22) in which the flight tube axis is perpendicular to the drift tube axis of the mobility cell. A pre-amplifier (25) amplifies the detector signal. A timing controller (28) synchronizes laser pulses and high voltage oTOF extraction pulses from pulser (31) with the detector electronics, which includes a constant fraction discriminator (34) and a time-to-digital converter (37). Data collection and analysis is performed using a computer (40). Data (FIG. 2) for fullerene-peptide mixtures show that the laser desorption mass spectra exhibit predominant peaks of sodiated- and potassiated-molecular ions. These additional peaks will help in the identification of the parent ions in cases where the analyte is in a biological milieu such as biological tissue. Adduct formation no longer hinders the mass spectral identification using MALDI-IM-oTOF since the adducted masses appear on different trends lines from the parent ion and its fragments in the IM-MS plots.

This use of adducts may be especially important when examining aerosolized bacteria or virus particles or intact cells in which only several types of biochemicals are predominant (e g proteins and glycans). In this case derivatizing or adducting with heavy elements such as Cs, Au, Ag, W or Pt can shift the density of the adducted bio-ion so that all of the adducts appear at different mobility/mass positions than would be the case for a non-adducted analyte of similar mass. Much of the behavior of the adducted analytes in the IM-MS systems is now more clearly understood such that the design of adduct probes which would specifically label portions of molecules is becoming feasible. Furthermore, the addition of specific elemental adducts allows enhanced post-ionization of neutral metal adducted analytes desorbed during the particle ablation by focusing and tuning a one, two, or three photon resonant or non-resonant photoionizing laser pulse at some time after the laser ablation event. The metal adduction is not critical for this photoionization step since non-adducted desorbed neutrals can also be photoionized in such a set-up, but the adduction does offers some advantages because the labeling efficiency of the adduct to a specific site may be well known and the photo-ionization cross-section of the adduct may be larger and better understood.

In another embodiment of the present invention, one can combine aerosolized matrices to an Ion Mobility-Time-of-Flight-Spectrometer. The possibility of MALDI at high pressures of up to 10 Torr has been demonstrated using a newly designed mobility cell, with collected mobility spectra having resolution of up to 60, and mass spectra with extremely low backgrounds of chemical noise with mass resolutions of 2500 for mobility separated test peptides. The ion mobility serves several functions in the present invention. A high pressure interface combines the ablation of the aerosol particle inside an ion mobility cell. After pulsed laser irradiation for example, the ablation plume is collisionally cooled within microseconds by interaction with the pure mobility carrier gas (e.g. helium or nitrogen (or air) at 1 to 10 Torr). The desorbed ions drift to the end of the mobility cell under the force of a high voltage field. Ion mobility separates ions according to their drift time determined by their charge to volume ratio. The second stage of the IM-MS system is the time-of-flight mass spectrometer with orthogonal extraction which provides continuous sampling of the ions transported through the mobility cell with the resolution of up to 2500 (or higher depending upon the MS design). The mobility drift times are typically several milliseconds while the flight times within the mass spectrometer are typically twenty microseconds or less. Therefore, several hundred mass spectra can be obtained after each laser pulse and stored individually. These spectra can be summed over several hundred laser shots so that the ion mass as a function of mobility can be measured. A unique data acquisition electronics and software allows then to collect the mass-shape information in 2-D.

Figure 2:
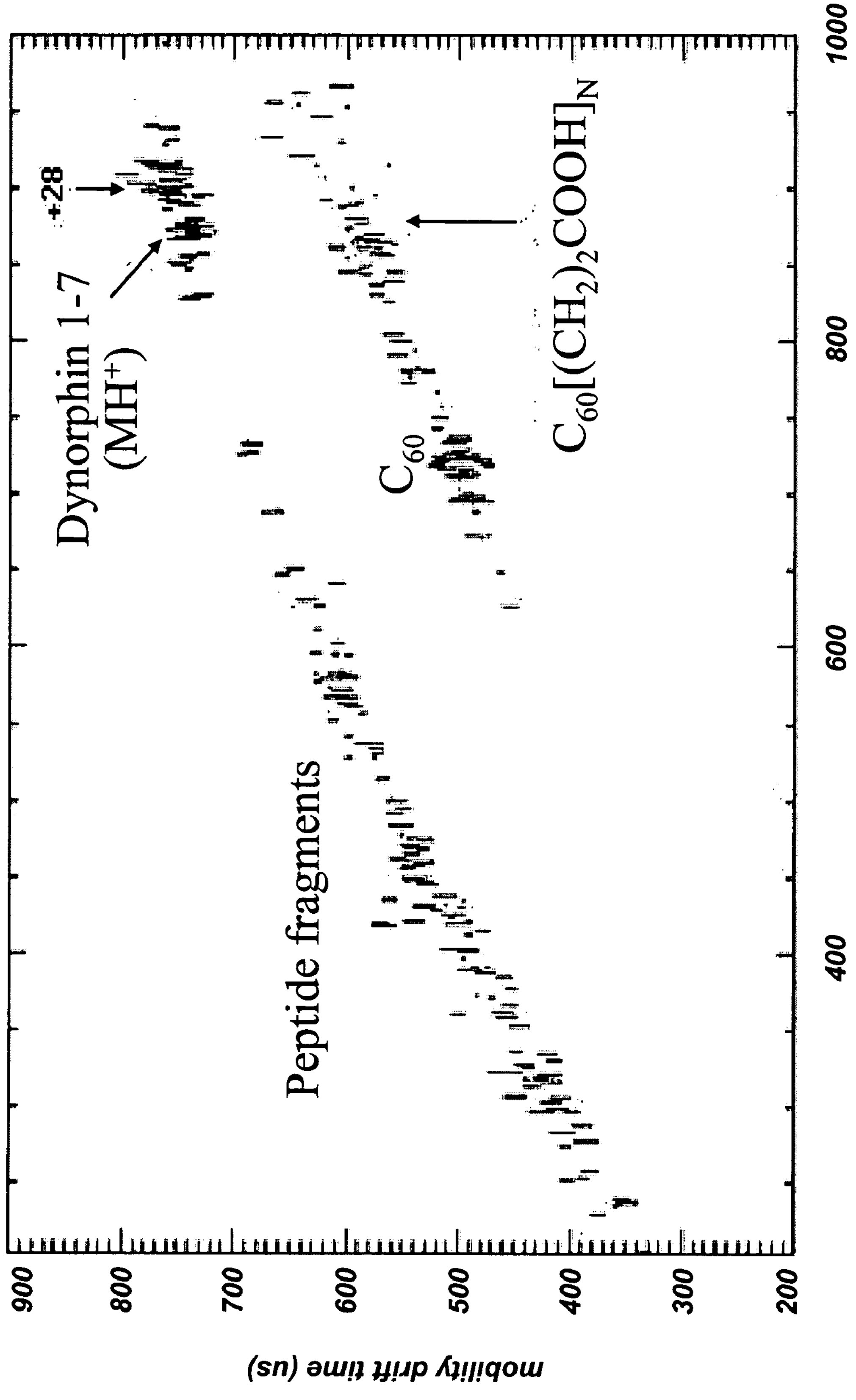
FIG. 2 is a mass-mobility 2D plot of dynorphin peptide analyte in a matrix of $C_{60}$ derivatized with $CH_2CH_2COOH$ side chains.

Matrix Assisted Laser Desorption and Ionization (MALDI) Mass Spectrometry of biomolecular ions was first demonstrated in parallel efforts by Tanaka using small metal particles suspended in glycerol (*Rapid Commun. Mass Spectrom.*, 2, 151 (1988)) and by Karas and Hillenkamp using organic matrices (*J. Mass Spectrom. Ion Processes* 78, 53 (1987)). In both cases, the matrix performs the dual function of both adsorbing the laser light and ionizing the non-light absorbing biomolecule through specific and poorly understood chemical reactions. $C_{60}$ and other species can be acid derivatized and used to comprise a MALDI matrix. The present work extends this concept and anchors the hydrogen-containing moiety on the carbon surface to which the peptide or protein is also adsorbed. The presence of hydroxyl groups or acid groups has the advantage of making fullerenes soluble in different solvents so that solutions of fullerenes with bio-molecules can be made prior to depositing thin films for MALDI mass spectrometry. The optical properties of carbon clusters also satisfy the necessary condition for a MALDI matrix of efficient absorption of the laser radiation. Moreover, another advantage of carbon-based matrices is that they permit the use of longer wavelength excitation sources including visible range lasers. Very low relative amounts of matrix (one molecule of matrix mixed with one peptide are necessary to achieve good signals from biological samples. This is in marked contrast to MALDI data from conventional matrix preparations which often require 1000:1 matrix/peptide ratio) for 1000 amu peptides. FIG. 2 shows data from a mixture of dynorphin peptide analyte and a matrix consisting entirely of derivatized $C_{60}$ with attached $CH_2CH_2COOH$ functional side chains. Laser irradiation causes the desorption of the molecular ion. Data also demonstrates that certain non-water solution-based derivatized fullerenes are useful as MALDI matrices for non-water soluble molecules such as lipids (example: cerebroside sulfate in a saturated solution of $C_{60}(C_{11}H_{23})_n$ in chloroform). Thus, one can aerosolize different portions of a biological preparation which has been solvent extracted (e.g. ether or chloroform soxhlet extraction) by introducing matrix particulates which are either soluble in the aqueous or organic phases and then creating MALDI aerosols from both solution phases.

It is possible to laser desorb intact bio-molecular parent ions from pure thin films of small peptides and proteins after implanting massive ion gold clusters at sub-monolayer equivalent doses. Initial SIMS work demonstrates that bombarding a pure peptide thin film with 10–20 keV $Au_{400}^{4+}$ ion clusters does not seriously damage the molecular structure of the peptide film. Based on these results, there is a technique which enhances two-dimensional MALDI imaging and allows three-dimensional depth profiling of biological tissues for the first time.

Figure 3:
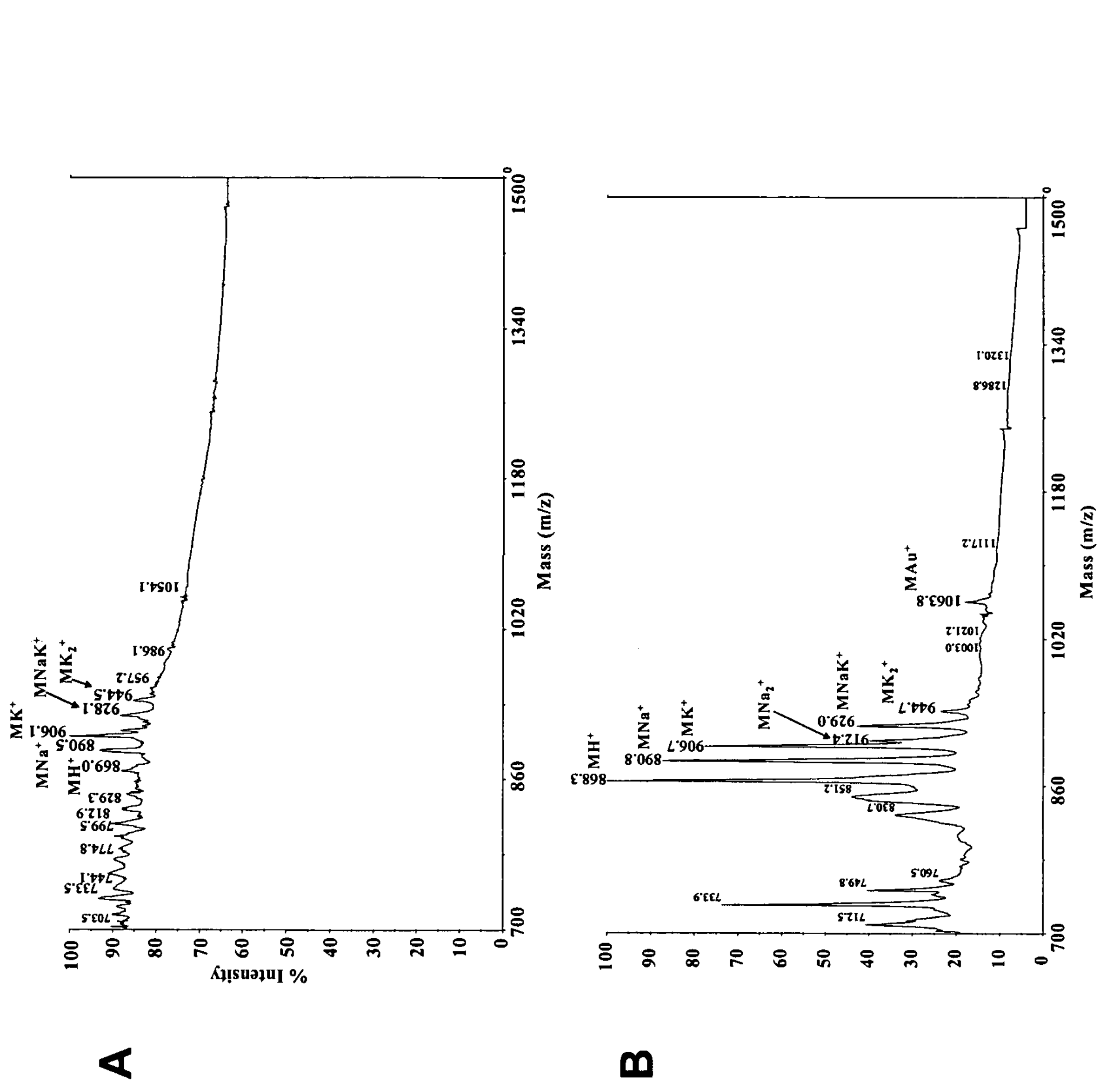
FIG. 3. Laser desorption mass spectra in positive mode at laser power of 2800 from (a) pure dynorphin 1-7 thin film; and (b) gold-implanted dynorphin film).

FIG. 3 compares the laser desorption positive mass spectra (obtained at a laser power of 2800) of a (A) control (100% intensity was 1050 counts) and (B) a gold-implanted ($1.7\times10^{13}$ $Au_{400}^{4+}/cm^2$) thin film of dynorphin 1-7 neuropeptide fragment; 100% intensity was 4400 counts) obtained with ABI DE Pro MALDI spectrometer using a nitrogen laser. The signals from the molecular protonated $MH^+$ (868) ion and alkali-adducts $MNa^+$ (890), and $MK^+$ (906) are much higher on the gold-implanted dynorphin 1-7 (the signal-to-noise is on the order of 200/1). Thus FIG. 3 clearly shows that the implanted gold clusters assist laser desorption of the peptide molecules. Using the apparatus pictured in FIG. 13, aerosolized particles including, but not limited to, gold could be ionized and accelerated into a solid sample (such as biological tissue) in a manner similar to the previous use of a liquid metal ion source to implant $Au_{400}^{4+}$ ion clusters into intact molecular peptide films. The results in FIG. 3 show that the similar nondestructive implantation of aerosolized nanoparticles in addition to gold will act as surface-localized matrices. The use of this scheme for implanting matrices solves an important problem for analyzing three dimensional structures and distributions of large molecular polymers in solids or in viscous condensed phases.

Figure 4:
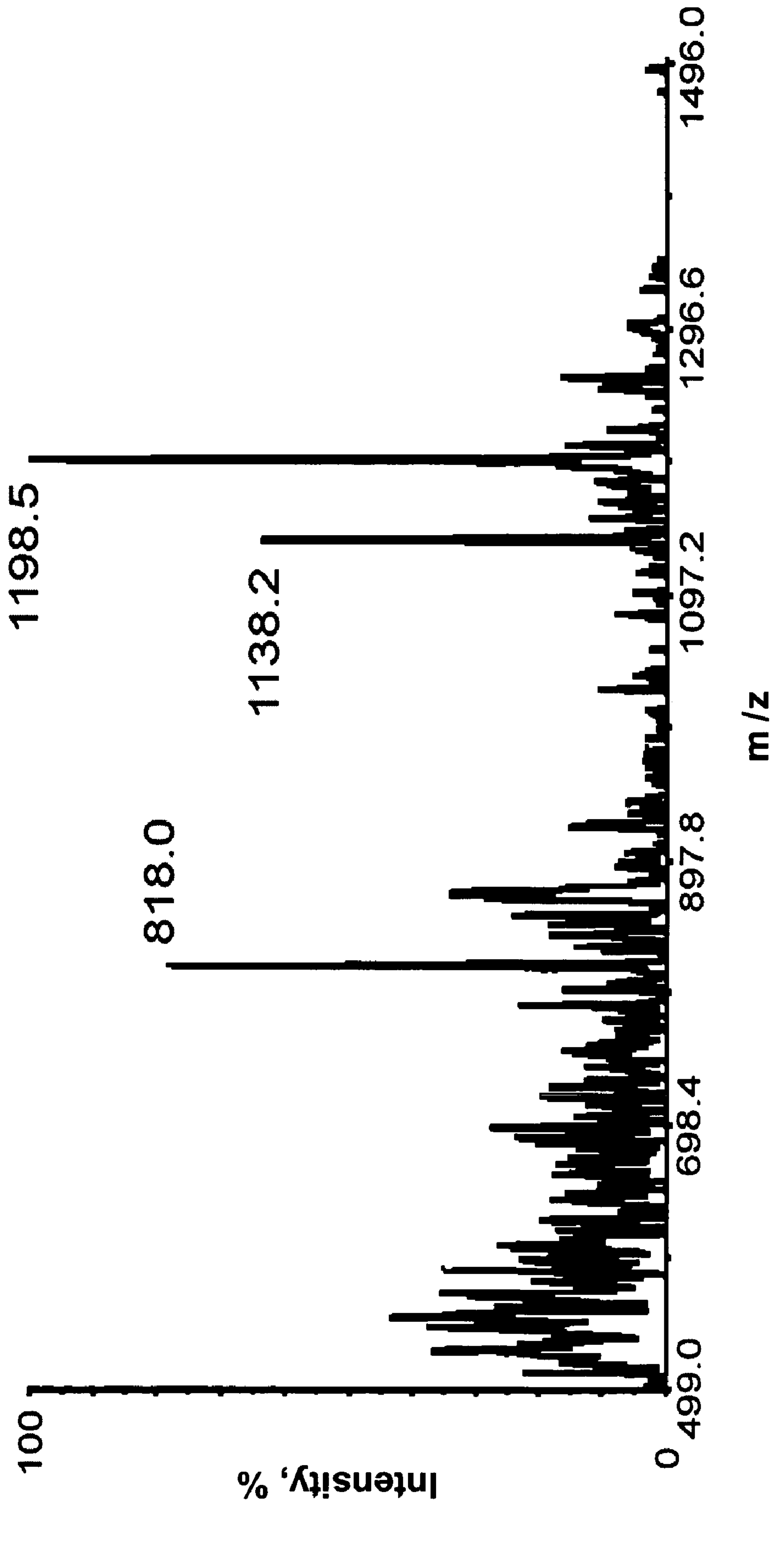
FIG. 4. MALDI spectrum of 3 peptides: RRPYIL (818.0 amu), dynorphin 1-9 YGGFLRRIR (1138.4) and VRKRTL-RRL (1198.5 amu), concentration of each peptide is 33.3 pmole (water solution); concentration of fullerene matrix 1 ng/μl (water-ethanol 1:1 solution).

FIG. 4 demonstrates a typical high vacuum MALDI spectrum of a mixture of three peptides; distinct peaks corresponding to $MH^+$ are observed with good signal/noise ratio with as little as one laser shot from loadings containing as little as two femtomoles of derivatized fullerene matrix. In contrast to the case of conventional organic matrices where high matrix/analyte ratios are needed in order to incorporate the analyte into the matrix crystal, the situation is reversed for $C_{60}$ based matrices. At higher matrix concentrations slightly higher peptide signal are obtained, but the spectra are noisier, and sodiated ions predominant. The increase in signal was not significantly larger as the ratio was increased to above 1/1. Almost absent at low matrix concentrations, the matrix signal appears strong compared to that of the analyte at higher matrix concentrations.

The quality of the spectrum in FIG. 4 is typical of that obtained routinely in one laser shot from as little as two femtomole deposited fullerene matrix. Unfortunately a two femtomole amount of matrix is physically difficult to find with the focused laser when loaded onto a 1 mm diameter stainless steel MALDI spot. The system shown in FIG. 5 allows us to overcome this limitation by aerosolizing the suspension of particulate matrix and analyte (45) (in this case a mixture of peptide and fullerene matrix). The particle formation device of FIG. 5 consists of a collision atomizer (40) which forms droplets (46) (of ca. 10 μm) diameter by flowing dry nitrogen (42) through the liquid suspension (42). These droplets (46) then enter a flow reactor (44) which dries the droplets (46) through evaporation of liquid through intermediate sized droplets (48) until dried aerosol particles (50) are achieved. The size of the dried aerosol particles (50), are determined by the ratio of the analyte:particulate: liquid and can typically be ca. 1.5 μm. These smaller dried particles (50) are then analyzed, typically in a ATOFMS (62) or preferably in the dual MALDI-IM-oTOF (60) shown schematically in FIG. 9.

Figure 5:
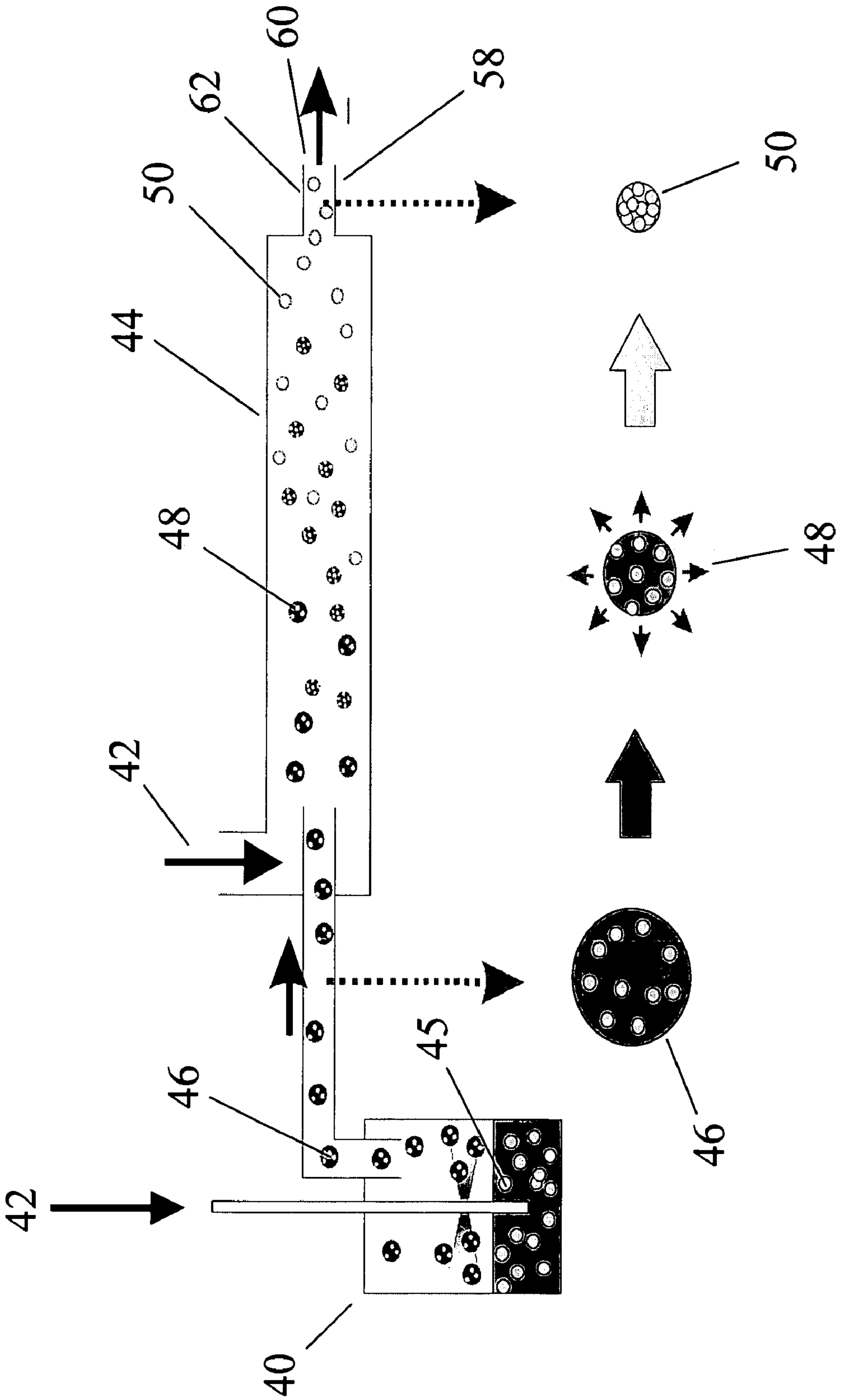
FIG. 5. Schematic of a solid particle formation device.
Figure 6:
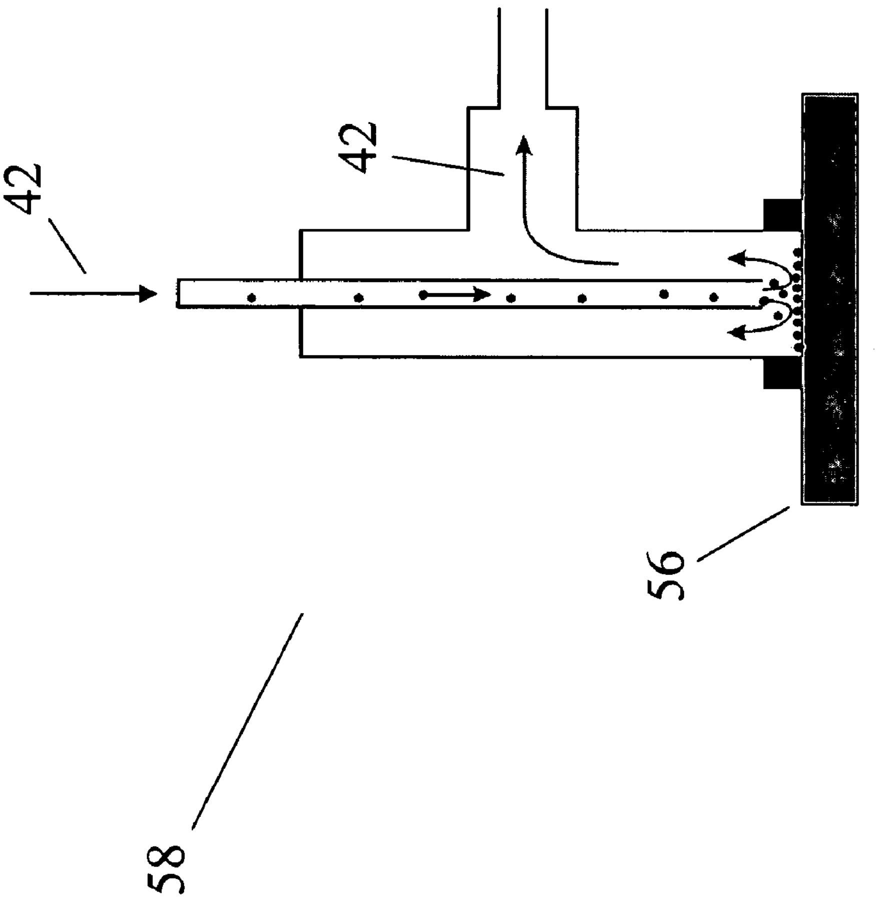
FIG. 6 is a schematic of the impactor and picture of the aerosol ring deposition on a standard 96 well MALDI plate.

The apparatus of FIG. 5 was used to feed an impactor shown in FIG. 6 where the particle stream can be directed into and impactor (58) where it can be deposited onto some substrate (56) which may for instance be a standard MALDI plate.

The apparatus in FIGS. 5 and 6 were used to demonstrate an example of this approach. First prepared separate aqueous solutions/suspensions of dynorphin and $C_{60}$ derivative (~4–10 mol/l) using HPLC grade water were prepared and later mixed together in desired ratios. The $C_{60}$ derivative solution/suspension was sonicated prior to the mixing. Mixed solutions (~10 mL) (45) were then atomized by using a home-made collision atomizer (40) to form droplets of the solution (diameter ~10 μm) (46). The composition in each droplet is the same with that in atomized mixed solution. To prevent contamination during the atomizing, ultra-high purity (UHP) nitrogen (42) was used for the atomizing with a flow rate of 1.2 L/min. The formed droplets were then introduced to a flow tube (ID 48 mm, length 1500 mm), where another flow of UHP nitrogen (42) (5 L/min) is added to let water in the droplets evaporate. Since both dynorphin and $C_{60}$ derivative are quite less volatile, both compounds do not evaporate and remain in the droplets (48) and upon drying (50). Solid particles (50) with the desired mixture of the matrix and analyte are formed after the complete drying. Particles with diameter smaller than 2.0 μm were formed from ~10 μm droplets (the particle size distribution was measured (not shown) and has a half width of around 1 micron).

The formed solid particles are then deposited onto a stainless steel MALDI sample plate. A gas/particle stream which contained solid matrix/peptide particles were injected into a thin steel tubing (OD ⅛", ID 1/16") where the gas/particle stream is accelerated. The accelerated gas/particle stream is then directed against to the sample plate. Since micrometer-size of particles have enough inertia, the solid particles can not escape from between the central acceleration tube and sample plate as do the gas molecules, but, instead, impact the sample plate and are thus deposited.

Figure 7:
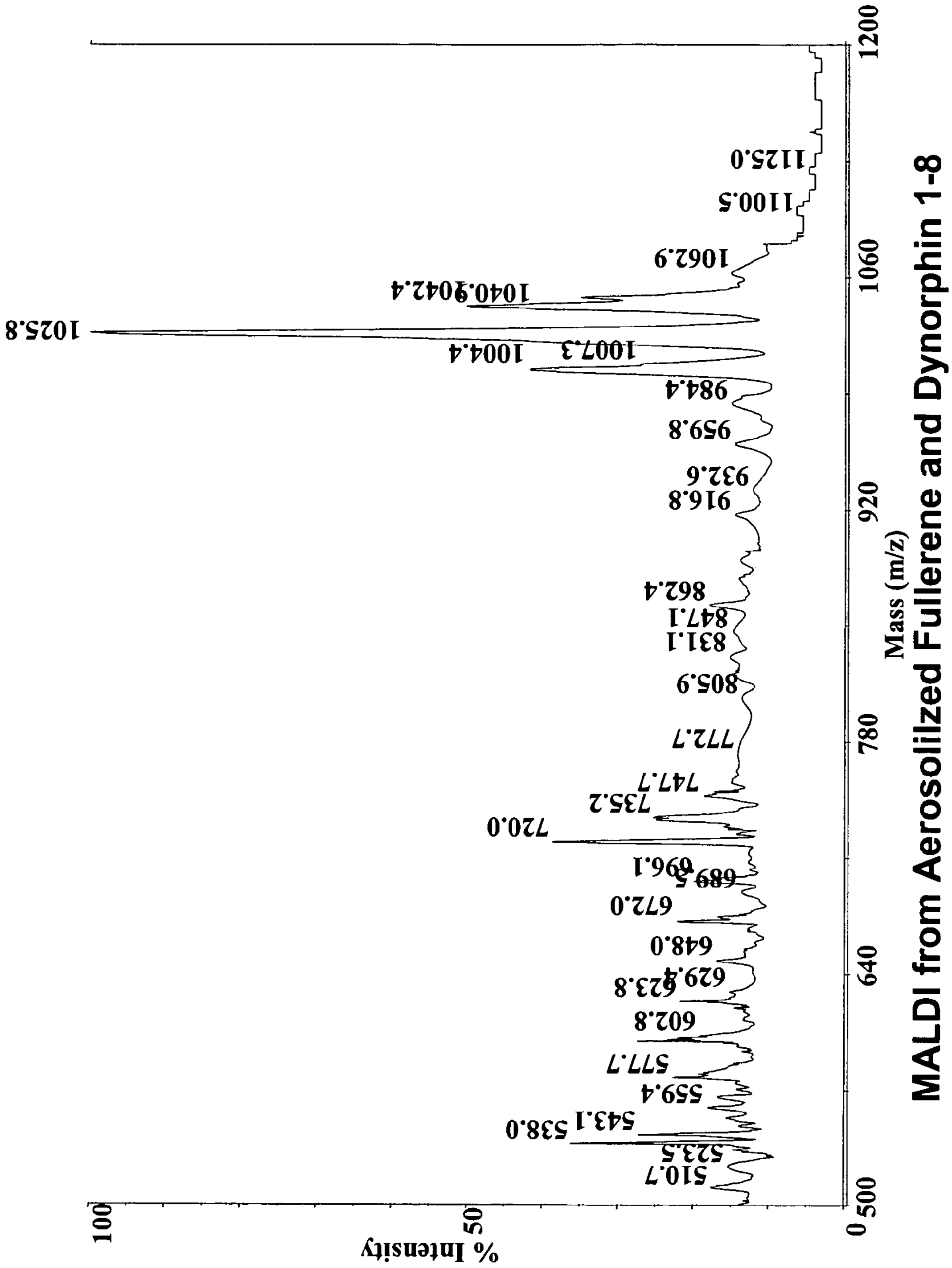
FIG. 7 is a MALDI spectrum from the deposited aerosolized particles shown in FIG. 6.

MALDI spectra shown in FIG. 7 from the standard 96 well stainless steel target plate shown in FIG. 6 were acquired from aerosols prepared from two different particle/analyte ratios (1:1 fullerene/dynorphin) and (5:1 fullerene/dynorphin). As long as the spectra were acquired from the regions which visually had the most accumulation of particles, then the ratio of matrix/analyte MALDI peaks was constant irrespective of where the laser was positioned on the collected aerosol sample. Interrogation of the areas showing less particle deposition and some stainless steel indicate variable intensities or in some cases no ionization at all. This indicates some amount of stainless steel substrate influence on the ionization of the peptide. This demonstrates that one can quantitatively prepare the aerosolized matrix/peptide particles and that if the substrate interaction is removed (by desorbing from thick areas of particles) then the MALDI intensities are quantitative. The data shows that new methods of quantitation can come from accurate preparation of the aerosolized matrix/analyte ratio and its ablation in a single particle mass spectrometer which totally eliminates substrate interactions.

Figure 8:
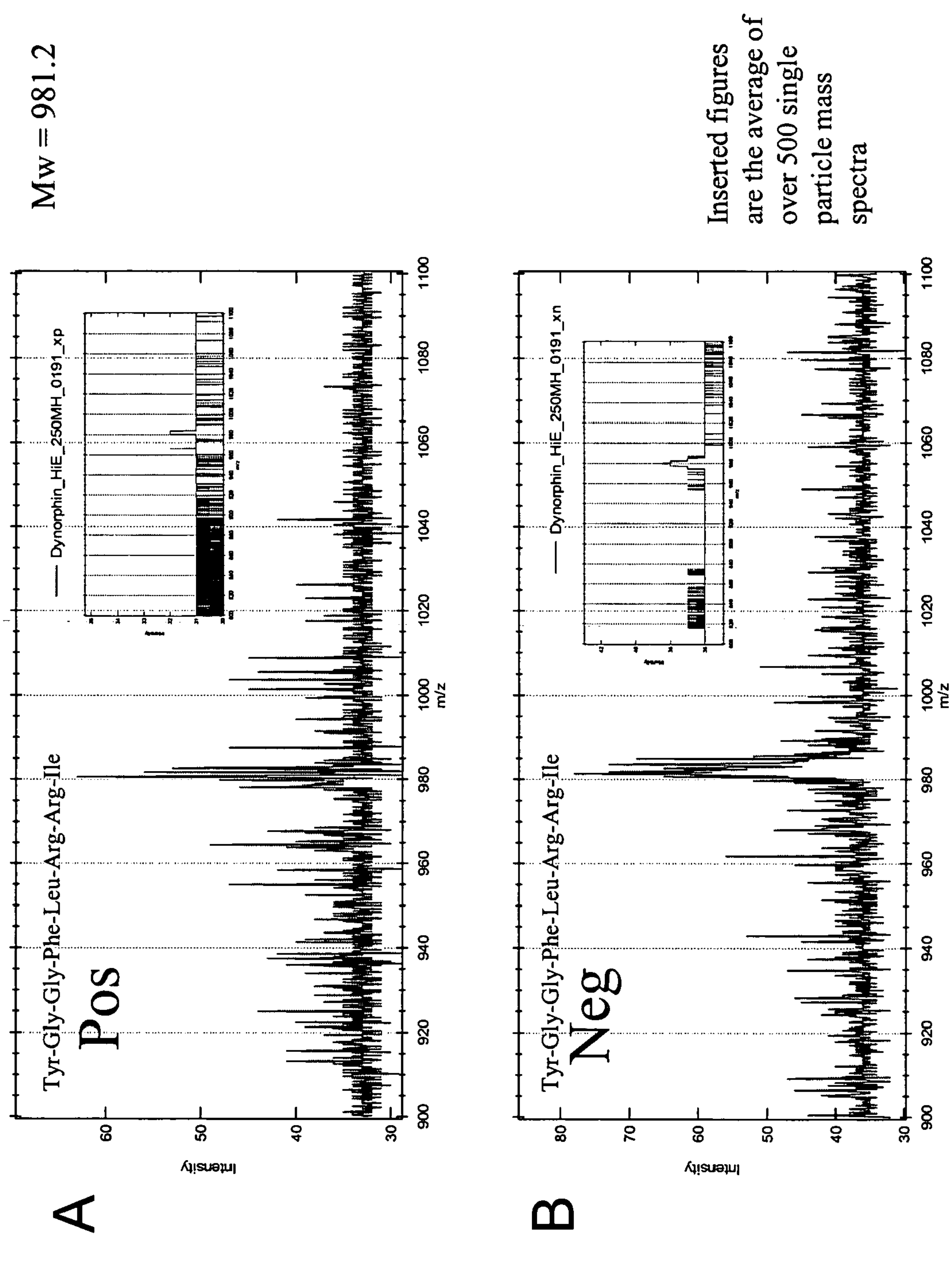
FIG. 8 are single particle spectra (a=+; b=−) from aerosolized particles generated with the apparatus of FIG. 5 from a pure solution of dynorphin 1-8.

For many applications the introduction of such specially prepared aerosolized matrices into an ATOFMS (62) where single particle ablation time of flight mass spectrometry is performed would make sufficient use of the sample preparations aspects of the present invention. ATOFMS is described in U.S. Pat. Nos. 5,998,215 and 5,681,752, both of which are expressly incorporated by reference as though fully disclosed herein. Single particle spectra from aerosolized particles generated with the apparatus of FIG. 5 from a pure solution of dynorphin 1-8 is shown in FIG. 8. The particle size after drying the 10 micron droplet to a solid particulate averages around 1.5 micron. This roughly contains around 100 attamoles of peptide. FIG. 8 shows a one shot spectra from one single aerosolized particle. The insert shows improved signal to noise if spectra from 500 such particles are acquired and averaged. The signal generated from the ATOFMS corresponds to a sensitivity for this peptide which is comparable to the sensitivity which could be attained if a high performance commercially available MALDI spectrometer had been used for dried droplet analysis.

However, as impressive as the performance of the ATOFMS for the single particle MALDI application is shown to be in FIG. 8, there are still some serious drawbacks to this instrumentation. The particle is ablated in vacuum and therefore has a large energy distribution of ejected ions which can only partially be compensated by well known reflectron mass spectrometer designs. Furthermore, the particles can be in various spatial locations when ablated which also limits mass resolution. Finally, although the ATOFMS does give simultaneous negative and positive ion spectra from each particle, each spectrum is still a one dimensional mass spectrum. Therefore, the analysis of a complex mixture shares the same problem of spectral congestion of analyte ions by matrix or biological ion interferences as do other one dimensional MALDI spectrometers.

Figure 9:
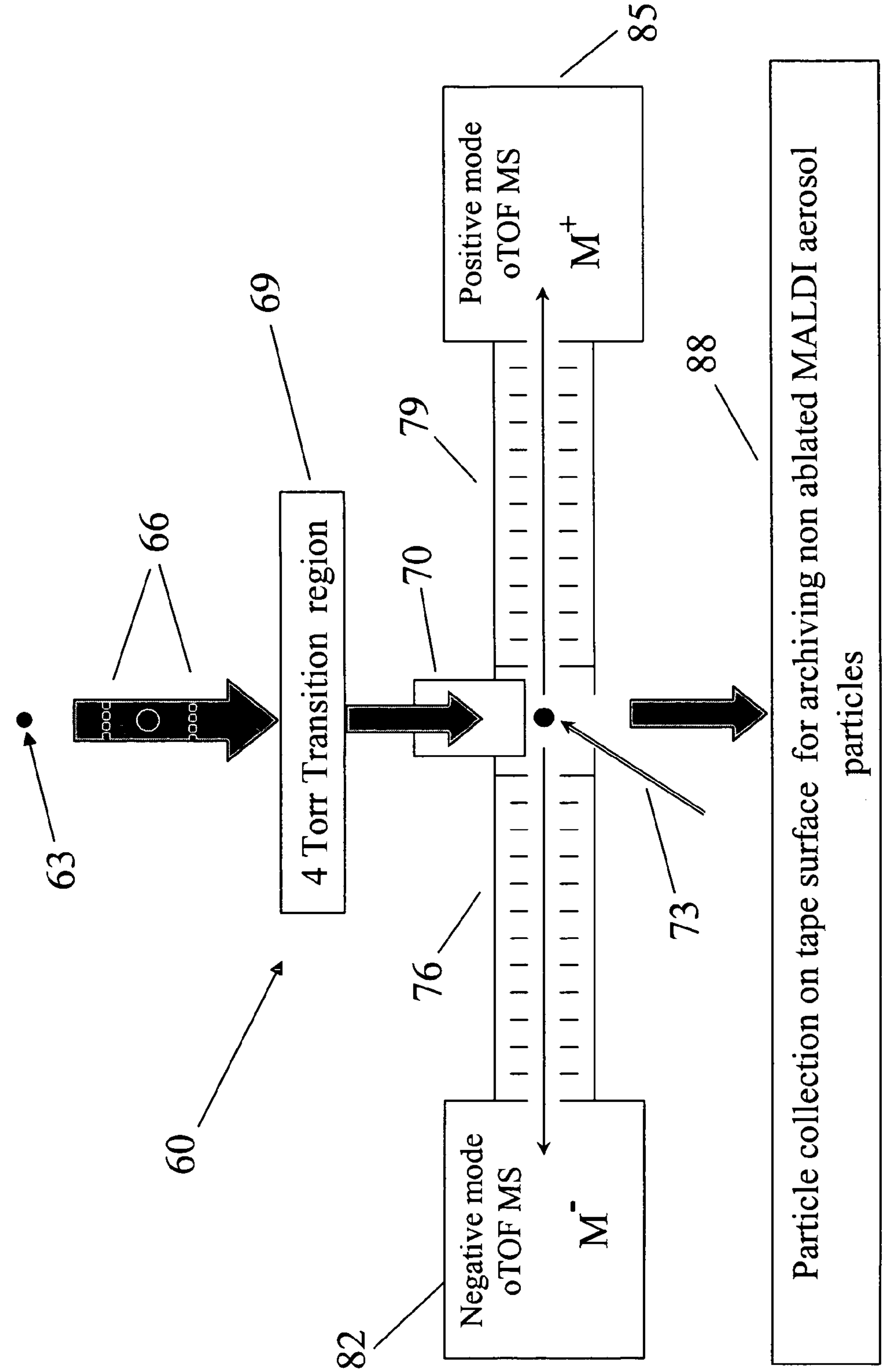
FIG. 9. Schematic of Dual IM-oTOF instrumental platform for performing simultaneous positive and negative mode ion mobility.

However, FIG. 9 schematically demonstrates another instrumental innovation of the present invention which overcomes the problems of the ATOFMS not only for single particle MALDI, but for micron size single particles in general. The aerosolized particles (63), matrix particles or aerosols are directly injected into dual ion mobility oTOF spectrometer (60) as shown schematically in FIG. 9 using any single particle injection schemes, including both those that are presently known and those to be developed in the future.

One example is a standard converging nozzle aerosol interface which has been used in the ATOFMS. The converging nozzle, which has poor focusing capability for ultrafine particles, nevertheless has excellent focusing for particle sizes between 0.5 μm to 1.0 μm. The velocity of a one micron particles (d=1 μm) is about 400 m/s when it leaves the nozzle and expands into a gas stream of 4 Torr He. Particles travel across the two centimeters of the mobility cell in approximately 50 μs, thus each particle will only be hit once with the 1 kHz laser. It may, however, be possible to hit each particle multiple times by pulse bunching the laser so that the particle can be hit with several pulses within a time window of 3 μs. This time frame for generation of the bio-ions would still enable maximum ion mobility resolution to be retained. The decoupling of the ionization at the beginning of the ion mobility cell from the mass measurement with the oTOFMS at the end of the mobility cell relaxes the requirements for the timing width of the laser or other ionizing source. The pulse duration needs only to be less than or equal to ca. 3 μs, but in some applications may be longer. This 3 μs ionization time is dictated by the maximum ionization pulse width which can still allow the ion mobility spectrometers to function with maximum mobility resolution. In FIG. 9, a generated 1 μm particle (63) is focused by an aerodynamic particle lens and nozzle (66) enters a 4 Torr transition region (69) and is introduced through a conductance limited tube (70; shown in FIG. 10) into a common sample introduction region of two mobility cells (76) and (79). This region is at 2 Torr. At this point, the particle is struck by ionizing radiation (73). The resulting ions are separated along one of the two mobility cell axes; negative ions to the left in FIG. 9 and positive ions to the right in FIG. 9 The ions are then detected in one of detectors (82) and (85) of the two oTOFs. For non-ablated or partially ablated particles, there is particle collection on a tape surface (88) for archiving.

Particle Introduction Interface

The MALDI aerosol sample particles which are prepared by mixing analyte and matrix are introduced from ambient pressure region into single particle MALDI system via converging nozzle followed by a differentially pumped vacuum stage. This particle introduction interface with the converging nozzle has been successfully developed and widely applied for ambient aerosol measurements. It was also experimentally shown that this converging nozzle configuration has optimum particle focusing capability for the particles with aerodynamic diameter of 1~1.5 and acceptable capability for the particle ranging from 0.2~2.5 μm.

Sample aerosol particles introduced into the first interface vacuum chamber (~4 Torr) through the converging nozzle are then accelerated due to super sonic gas expansion upon the pressure drop. The particles in the gas stream are also focused by the nozzle and particle beam, which improves the particle introduction efficiency to the mobility analyzer/mass spectrometer region and thus measurement efficiency. Arrival of the particle to the mobility analyzer may be optically determined by measuring laser light scattered from the particle with a photomultiplier tube (PMT) and this particle detection scheme may be used to synchronize firing a desorption/ionization laser to shoot the particle of interest. The first vacuum region may be pumped by mechanical rotary pump (300 L/min) and foreline trap inserted between the vacuum chamber and the rotary pump to prevent contamination from the rotary pump.

A pressure of about 4 Torr may be achieved at the first vacuum. At this pressure region, the particles with 1 μm diameter do not suffer excessive friction from surrounding gas. Nevertheless, the preferable design calls for the transition region between the nozzle and the mobility cell to be as short as possible. The diameter of the nozzle opening is preferably about 0.342 mm and the particle beam should not expand beyond this volume when traversing the ion mobility cell.

Figure 10:
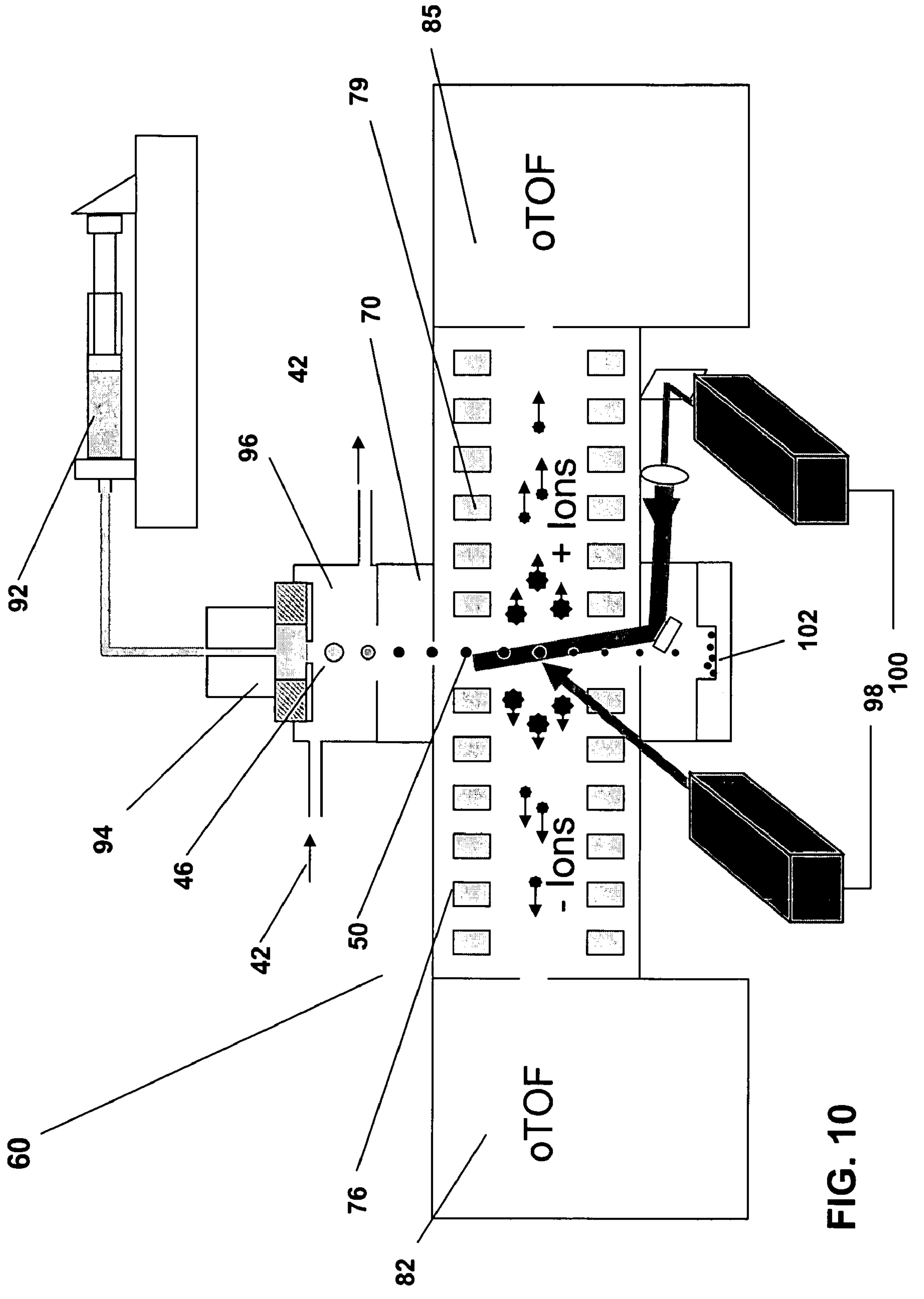
FIG. 10. Schematic of instrument containing a vibrating orifice solution aerosolizer.

The interface can be attached to a single stage mobility instrument as that shown schematically in FIG. 1, or it can be used with the dual MALDI-IM-oTOF such as that shown in FIGS. 9 and 10. Each 1 μm diameter particle will contain about 100 attamole of matrix and about 100 attamole of 1000 Da peptide. As an alternative to recording only single spectra from single particles, one can average laser shots from 10–1000 (or greater) of these particles for increasingly more detailed and accurate MALDI spectra. The use of the single particle aerosolized dual MALDI-IM-oTOF technique can extend the type (oligonucleotides, protein, lipids) and size of molecules (larger than 5000 amu) that can be analyzed with single particle laser ablation. The incorporation of derivatized gold clusters (or other metal cluster) for example can make possible the analysis of pure peptides, proteins, oligonucleotides and lipids and their mixtures through aerosolized single particle matrix techniques followed by analysis with the dual IM-MALDI-oTOF MS. Molecular ions of small pure peptides and insulin after implantation with 10 keV massive gold clusters implantation have been desorbed and detected. This can also be done with the fullerene matrices applied to larger pure peptides, proteins, oligonucleotides and lipids. The following peptides can be used for test illustration of the general applicability of the instrumentation and aerosolized single particle matrix technique but are meant for illustration only. These molecules would comprise dynorphin fragment 1-8 [YGGLFRRI], gastrin [LEEEEEAYGWMDF-$NH_2$], sulfated gastrin [pEGPWLEEEEEAY($SO_3H$)GWMDF-$NH_2$] and [SVLpYTAQPN]. The following lipids can be used: lipid A monophosphoryl, sphingomyelin and cerebroside sulfate, and as nucleotides: CATG, CATGA and CATGAT. Droplets of pure peptide, protein, and lipid solutions are aerosolized with the fullerene test matrix and deposited both on stainless steel plate and air-dried as well as introducing them into the particle spectrometer. The deposited samples can be analyzed with conventional MALDI and/or MALDI-IM-o-TOF MS. In the mass spectra, we monitor not only the parent ion peaks (protonated and alkali-adducts) but also the fragments, matrix fragment adducts. One can also verify with IM-oTOF that the protonated molecular ions ($MH^+$) and the alkali-adducts ($MNa^+$ and $MK^+$) lie on two separate mobility trend lines and can thus be separated as it has been seen for angiotensin II. Tests could also be conducted with, inter alia, Lysozyme, which is protein of ca. 17 kDa.

Use of VOAG for Injection of Liquid Solution or Dried Matrix/Analyte Droplets Into Dual MALDI-IM-oTOF As shown in FIG. 10 any liquid sample solutions (92) can be directly and efficiently introduced to the dual MALDI-IM-oTOF (60) using a vibrating orifice aerosol generator (VOAG) (94). The VOAG (94) is directly interfaced to the IM cell through optional drying (96) and/or pressure adjusting chamber (70). The VOAG technique has been used for many years to produce very uniform size of droplets (46) or particles (50) dried from droplets in the field of aerosol research. This direct droplet introduction technique requires much lesser amount of sample solution compare to other particle/droplet preparation methods based on nebulizing and atomizing of the solution. Less than 1 mL of sample solution is enough for the analysis. The efficient coupling of aerosolized liquid to mass spectrometry or into the dual IM-oTOF allows for direct coupling for the first time of the output of a liquid chromotograph (LC) (which would replace the syringe pump (92) pictured in FIG. 10) to an improved dual MALDI-IM-oTOF. It is within the scope of this invention to co-mix the eluent of the liquid chromatogram with a matrix solution just before or within the VOAG device prior to aerosolization of the solution. The solvent "dead" volume within the VOAG can be minimized so that high LC chromatographic resolution is retained. Traditionally, an LC has been coupled to a mass spectrometer through the use of Electrospray Ionization (ESI). By contrast, our embodiment would advantageously decouple the droplet formation with the VOAG from the subsequent MALDI ionization step and would advantageously then also provide simultaneous IM-oTOF of both positive and negative desorbed ions. One may also use multiple lasers for desorption and ionization of the particles. FIG. 10 shows two lasers so positioned so that one laser (100) can desorb the analyte from the particles and the other can effect an ionization pulse (98). Such a sequence can be an advantage if the particles still contain some solvent so that the desorption energy can be directly coupled into the solvent. Such a sequence might be with an infrared (IR) laser coupled into water solvent followed by and ionization pulse from and excimer laser into the gaseous ablation plume from the IR desorption of the particle. Other sequences in which the laser is designed to interact with the co-mixed particulates followed by an ionization pulse tailored to the analyte are possible.

As the vibrating head of the VOAG vibrates, droplets, having diameters which are nearly the same as the opening of the orifice attached to the vibrating head, are ejected from the orifice. As the head vibration is repeated, a droplet train in which each droplets are exactly separated both in space and in time, is formed and travels into the drying chamber and/or pressure adjusting chamber if necessary. The spacing of the droplet (and number of droplet produced per time) is controlled by changing frequency of the vibration. This very controlled droplet/particle train allows one to synchronize laser firing to shoot each droplet/particle in the middle of ionization region without optically tracking the particle.

If a drying chamber is used, then the droplets are dried and the resulting solid aerosol particle consists of non-volatile solute which can be either directly dissolved in the droplet solvent or, in the case of larger molecules, may be suspended or in the form of micelles within the droplet prior to drying. After dried particles are formed, the particles travel into IM cell. In the middle of IM cell, each droplet or dried droplet (solid particle) will be desorbed and ionized—one by one—using an ionization source which may be a laser or lasers(s) or may be an infrared heat source. The chemical composition of each particle is analyzed with a dual polarity IM-oTOF mass spectrometer. The desorption/ionization source may also comprise any other energy source suitable for the same purpose known to those of skill in the art, including, but not limited to, electron beam sources, charged particle sources, metastable atom beams, etc. These may even include sources to be developed in the future such as X-ray lasers. When charged particle beams are used for ionization (or when charged aerosols—FIG. 13—are being injected into the dual IM-TOF it may be necessary to keep the ablation region between the two ion mobility cells at ground potential during the ionization and thereafter pulse them to appropriate high voltages to extract ions into the dual IM cells.

By using a coaxial laser irradiation configuration where laser light is directed coaxially or nearly coaxially to the aerosol particle or droplet or more specifically to a particle or droplet stream, multiple droplets/particles in the stream can be analyzed with each laser shot. In comparison to an orthogonal laser irradiation configuration which intersects one droplet at one position with one laser pulse, the coaxial desorption/ionization laser light has a much larger cross section with the droplet/particle stream. Therefore the laser does not need to be fired with higher accuracy of timing, which results in a much simpler timing circuit. This multiple particle analysis improves particle detection efficiency, and thus result in higher sensitivity and shorter analysis times. Alternatively, multiple lasers can be used to fire when a droplet is at a specific position so that a higher throughput can be achieved. This will be an even more important embodiment in he future, as powerful wafer level solid state lasers emerge so that laser arrays can be positioned and programmed to fire into the ablation region to hit multiple droplets either simultaneously or sequentially.

The VOAG system may, for example, generate droplets at the rate of up to 10 MHz while some desorbing and ionizing lasers can only operate at several kHz. Thus, some parallel ionization and use of multiple channels of ion mobility/mass spectrometry may be necessary in some cases. One such incarnation which can be understood in reference to FIG. 10 and from our earlier patents and patent applications specifying multi-aperture anode periodic focusing ion mobility spectrometers would be as follows. Examples of such ion mobility spectrometers are given in U.S. Pat. No. 6,639,213 and co-pending U.S. application Ser. No. 09/798,030, both of which are expressly incorporated by reference as though fully disclosed herein. The droplets are produced in a burst mode to fill the gap region shown schematically in FIG. 10 which for example might be 30 cm. Thus with drift times of the particles around 400 m/sec we could adjust the droplet production rate of the VOAG so that 10 droplets at 3 mm spacings are present in the ablation region between the two mobility spectrometers. The mobility spectrometers can be constructed so that multiapertured electrodes with hole spacings of ca. 3 mm and hole diameters of ca. 1.25 mm would be opposite this region and arranged so that the ten droplets would be exactly in front of each of the channels created within the ion mobility cell by the registered multiaperture ion mobility anodes. Thus in our example ten ion beamlets would be generated after ten simultaneous firings of ten lasers directed at each droplet location (or one coaxial laser (100) pulse traversing all ten particles or one pulse from an orthogonal laser (98) focused into a line source which would simulatanesouly impinge multiple particles) and each ion beamlet would be extracted into the ion mobility cell. Each beamlet remains separated by the focusing action of the multiple apertured electrodes as the ions traversed the ion mobility cell. The beamlets would emerge into the oTOF region and could be focused so that the ion beamlets retained their registry with the droplet from which they came even as the ions pass through the oTOF and onto a position sensitive anode in the mass spectrometer. Thus in addition to improving the throughput of the analysis, the differences in concentrations of reactants within the droplets could be determined with a time constant of around 10 microseconds. Another application of this scheme would be as follows: as each aerosol particle comes adjacent to an aperture within the ablation region it is impinged with an energy source so that the particle is only partially ablated. Thus in our example above, one aerosol particle would be reduced in size in front of each of the 10 hole spacings. In this way, the material which is ablated enters sequentially each of the ten apertures and is thereafter analyzed sequentially by the IM-oTOF equipped with a position sensitive detector which keeps each of the 10 IM-oTOF chromatograms correlated with each aperture. In this way the surface of the aerosol is sequentially peeled away and analyzed in each of the 10 ablation steps so that the depth distribution of elements and molecules can be determined from each single aerosol particle. By multiply impinging (i.e., impinging the particulate more than once) the nanoparticulate or particulate sample with an energy source (such as, for example, a laser, a pulsed X-ray source, a chopped continuous infrared source, a pulsed electron beam source, or other appropriate source) we achieve a "peeling away" of the sample which allows one to perform a depth profile analysis.

The introduction of liquid droplets directly into the dual MALDI-IM-oTOF allows solution phase chemistry to be monitored by using water directly as a matrix. It is well known to those skilled in the art that IR lasers can be used to generate MALDI from water isolated analytes. It is therefore not necessary to pulse a laser; a continuous intense IR source which can be modulated on and off after a few microseconds may be a preferable way to generate the ions from water (or other solvent) droplets. Furthermore, the temperature of the entire assembly can be controlled so that the droplets are in equilibrium with the partial pressure of gas. In the case of water this could mean that the entire ion mobility apparatus could be filled with a few Torr of water, or a mixture of water and helium, and that the water vapor would act as the carrier gas for the ion mobility measurement. Furthermore, previous work in the field has demonstrated combinations of mobility cells which allow interfacing to atmospheric pressure ionization. Therefore, combinations of mobility cells could be used to collect ions which were created within the region labeled "droplet drying region" in FIG. 10. This can be a near atmospheric pressure region and several new mobility cell designs have been recently disclosed which work well in this pressure regime. In addition, for some cases, the creation of ions is more efficient at these higher pressures and the new IM cell designs can be used with greater efficiency to transport ions from an atmospheric pressure ionization ion mobility region into a lower pressure mobility cell which serves to gradually interface the higher pressure region into the high vacuum region of the mass spectrometer.

Other mixture combinations of solvents with water or other solvents by themselves may be usefully employed in this device. A particularly important embodiment of this technique would be the aerosolization of individual cells or the use of a cell sorter to input intact cells into the dual-IM-oTOF. Also an important embodiment would involve aerosolization of previously airborne cells (e.g. from a cell sorter) or pathogens (such as a bacteria or virus) which had been first collected in a condenser apparatus wherein they are mixed with matrix (either particulate and/or conventional matrices). Prions are another example of possible pathogens. The pathogen which is suspended in the collector liquid (to which soluble matrix might also be added) is aerosolized into the MALDI-IM-oTOF. The VOAG orifice size would be chosen to produce a droplet which would on average contain only one pathogen or cell particle. The laser ablation of the particle will not only create ions but will also induce molecular and elemental fluorescence processes which can also have signatures related to the type of pathogen or cell. If the single particle fluorescence is correlated with the mass and chemical type identification given by the IM-oTOF spectrometry from the same particle, unique signatures can be obtained which are more specific for a particular type pathogen than could be obtained with the use of just one or the other of the techniques alone. The high repetition rate of the VOAG (up to 10 MHz production of droplets) coupled with these parallel correlated detection schemes allows many single particle correlations to be rapidly made and thus makes the detection of low levels of pathogens practical in a reasonable time scale. Any correlation between the fluorescence and IM-oTOF data could be determined, for example, by a computer.

While the above example was given for pathogen detection by correlation of fluorescence with IM-oTOF data, the detection of other types of aerosol particles could also benefit from the simultaneous comparison of the two techniques on each and every particle. Moreover, other simultaneous measurements combinations are also possible. For example, existing and newly emerging X-ray lasers could be used to irradiate the particles at high repetition rates and with monochromatic radiation so that a variety of simultaneous measurements could be made even before performing the dual IM-oTOF or dual MALDI-IM-oTOF. Depending on the energy of the X-rays, the result may be X-ray induced fluorescence or it may result in the emission of core level electrons from the outermost elements on the aerosol particle. The time of flight of these photoelectrons can be efficiently measured by special position sensitive detectors having high bandwidth and high timing resolution (see PCT/US02/40877 claiming priority to U.S. application Ser. No. 10/025,508; these are expressly incorporated by reference as though fully disclosed herein). As is well known to those skilled in the art, the intensities of these time-resolved photoelectrons can be related quantitatively to the elemental stoichiometry in the outer surface layer of the particle and the chemical shift of the photoelectrons is related to the different chemical binding state of each element. Acquisition of such information has not, heretofore, been considered possible from single aerosol particles; however, with the advent of new detection technologies, coupled with the X-ray laser or advanced pulsed high energy photon sources, these measurements are indeed practical. Likewise, inducing X-ray or fluorescence emission useful in characterizing elemental composition from entire single particles can be obtained by impinging pulsed or quasi-continuous electron beams onto the particle. Such sequences can be followed by ablation of the particle or by photoionization of the vapors released from the particle surface by subsequent laser irradiation. Correlation of each of the independent data with the subsequent IM-oTOF can be useful in a variety of applications such as characterizing the surfaces of environmental aerosols for types of adsorbed organic or organometallic pollutants to identification of airborne cells or pathogens as well as the characterization of nanostructured nanoparticulates which may be useful as electronic or structural materials having dual use either within or outside the scope of biological applications. It is furthermore, within the scope of this invention to apply such surface or bulk analytical techniques to the sequential ablation of a single aerosol particle as the particle passes in front of each aperture of a multi-apertured IM cell such as those described previously herein.

Figure 11:
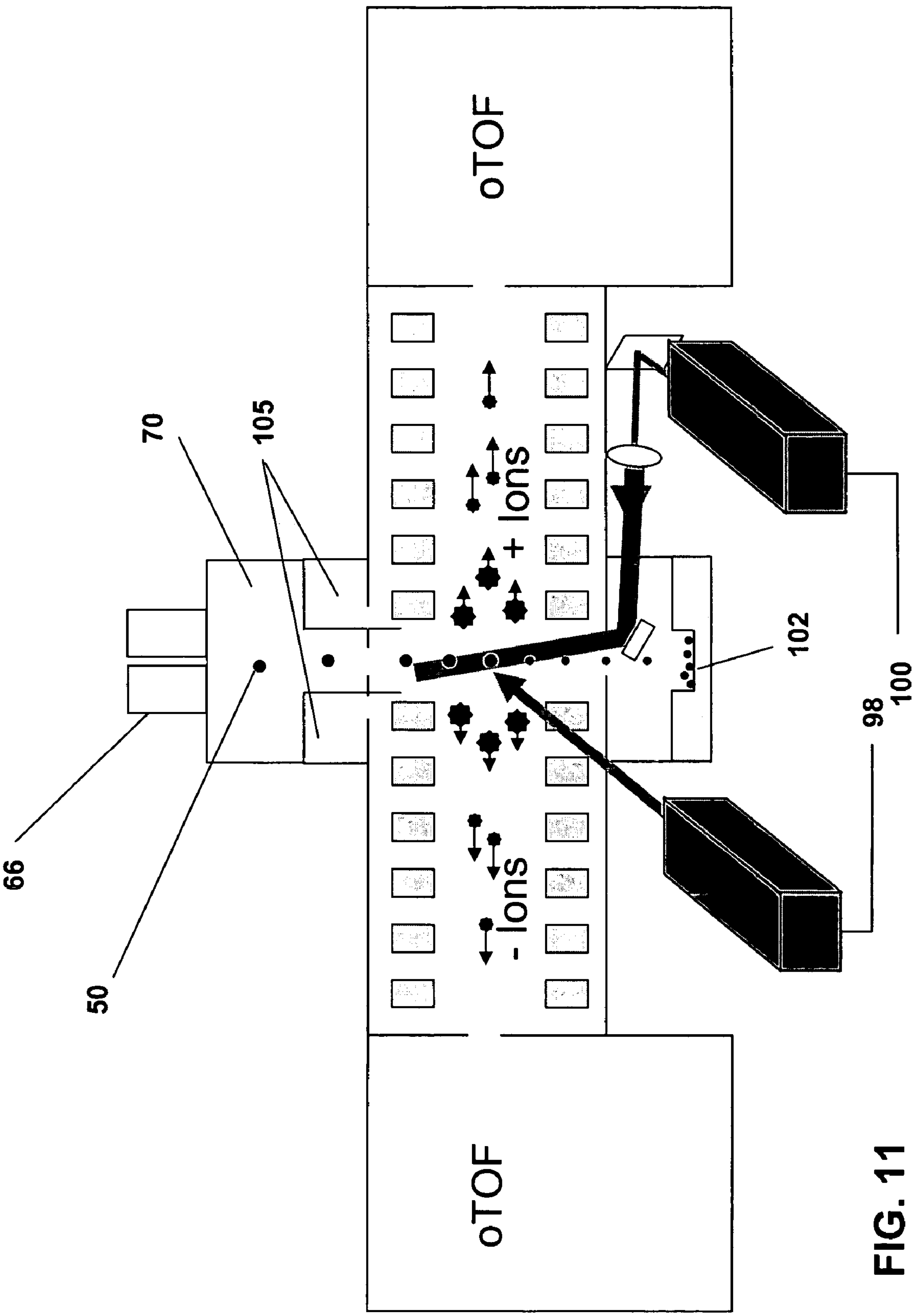
FIG. 11 shows an instrumental configuration which allows introduction of aerosols smaller than a few nanometers into the dual IM-oTOF.
Figure 12:
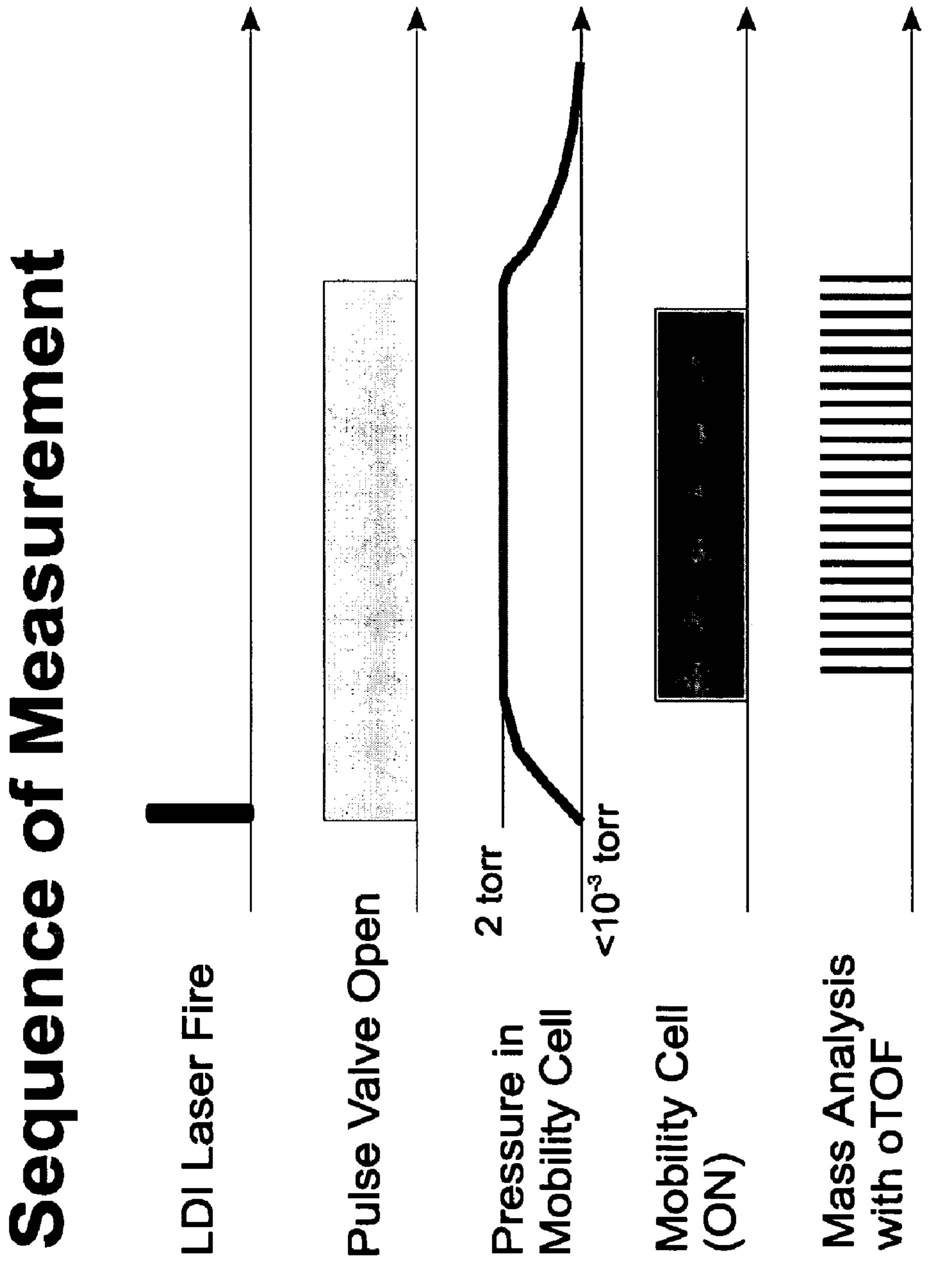
FIG. 12 gives an example of a timing scheme that can be used in the FIG. 11.

FIG. 11 shows an instrumental configuration (a variation of FIG. 10) which allows introduction of aerosols smaller than a few nanometers into the dual IM-oTOF. These particles may be environmental aerosols sized by an aerodynamic lens (66) or they may be small particulates generated by the VOAG of FIG. 10 from very dilute solutions so that the analyte and matrix when dried comprise nanoparticulate sizes of a few 100 nm. For these sized particles to effectively get into the ablation region between the two ion mobility cells, the pressure in this region must be on the order of a few tens of mTorr. One way to achieve this is by the use of pulse valve (105) He introduction so that the pressure in the mobility cell is high only when needed. Thus nanoparticulates can be optically tracked into this region and the helium pulse timed so that the gas arrives when the ablation is about to occur. In combination with (or in place of) the use of the pulsed He, we can construct special differentially pumped inlets into the ion mobility spectrometers (examples of which are given in U.S. Pat. No. 6,639,213 and co-pending U.S. application Ser. No. 09/798,030 (filed Feb. 28, 2001), both of which are expressly incorporated by reference as though fully disclosed herein). These differential pumping schemes incorporate multiaperture anodes to maintain a higher pressure region in the mobility cell and still obtain lower pressures in the ablation region. This allows the nanoparticles to be injected even without the pulsed helium scheme. Alternatively, the helium can be distributed into the mobility cells through a gas manifold (105) which also comprises two (or more) pulsed helium valves as shown in FIG. 11. The injection of helium could alternatively be controlled by one or more piezoelectric microvalves located with their output directed into various portions of the ablation region and even within the mobility cell. These valves would not have to be a full closure type and thus a very high frequency pulsed sequence could be used to rapidly impose a desired gas phase profile which could be desirably synchronized with the introduction of the nanoparticle and its subsequent ablation. One such timing scheme is shown in FIG. 12 using the valve shown in FIG. 11. It should also be readily apparent that the optical output of the desorption (or desorption/ionization) source (98) can be defocused into a line which would simultaneously intersect many droplets or particles traversing the region between the mobility cells pictured in FIGS. 10 and 11. Also, the incorporation of a heated substrate of an appropriate material (molybdenum or tantalum are some non-limiting examples) coupled to or within the dual IM-TOFMS to thermally ablate and vaporize the particles (in either configuration shown in FIGS. 10 and 11) followed by any known method for ionizing the released vapors (or smaller nanoparticulates ablated from the hot surface) is also within the scope of the invention.

FIG. 13 shows an instrumental scheme (with two variations illustrated as A and B) in which elements within vacuum systems are fluidly coupled for generating aersol nanoparticulates (110), charging the nanoparticulates (115), selecting the nanoparticulate size (66 and 118), accelerating the charged nanoparticulates (120), focusing the charged particulates (125) and injecting them into a viscous liquid or a solid surface located on a sample manipulator (see (1) in FIG. 1). Nanoparticles are charged by a charging device, focused by lenses, and accelerated such that they bombard a target sample and are implanted in the sample. The variation illustrated in FIG. 13A uses an aerodynamic lens to select the nanoparticulates, while that in FIG. 13B shows another possible arrangement of fluidly coupled elements in which a differential ion mobility spectrometer (118) is substituted for the aerodynamic lens and is used to select the nanoparticulates and inject them onto a solid (1) or into the dual IM-TOFMS (60). This method of particulate implantation would complement the operation of MALDI-IM-oTOF spectrometer designs which have been previously disclosed.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications mentioned in the specifications are indicative of the levels of those skilled in the art to which the invention pertains. All patents, published patent applications, and publications are herein incorporated by reference to the same extent as if each individual publication was specifically and individually indicated to be incorporated by reference.

1. U.S. Pat. No. 6,639,213, issued Oct. 28, 2003.
2. U.S. patent application Ser. No. 09/798,030, filed Feb. 28, 2001; published Oct. 25, 2001 as Publication No. 20010032929A1.
3. U.S. Pat. No. 6,683299, issued Jan. 27, 2004.
4. U.S. patent application Ser. No. 10/689,173, filed Oct. 20, 2003; published Jun. 17, 2004 as Publication No. 2004-0113064 A1.
5. Tanaka, K., Waki H, Ido Y, Akita S, Yoshida Y., Yoshida T., *Rapid Commun. Mass Sectrom.* 88, 2, (151).
6. Karas M., Bachman D., Hillenkamp F., *Int. J. Mass Spectrom. Ion Processes* 1987, 78, (53).
7. Schurenberg M., Dreisewerd K., and Hillenkamp F., "Laser Desorptioin/Ionization Mass Spectrometry of Peptides and Proteins with Particle Suspension Matrixes," *Anal. Chem.* 1999, 71 (221–229).
8. R. Taylor, Lecture Notes on Fullerene Chemistry: A Handbook for Chemists. Imperial College Press: London, 1988.
9. K. J. Gillig, B. Rutolo, E. G. Stone, D. H. Russell, K. Fuhrer, M. Gonin, J. A. Schultz, "Coupling High Pressure MALDI with Ion Mobility/Orthagonal Time-of-Flight Mass Spectrometry," Anal. Chem. pp. 72, 3965, (2000).
10. A Study of Peptide-peptide Interactions Using MALDI Ion Mobility o-TOF and ESI-TOF Mass Spectrometry, A. S. Woods, J. Koomen, B. Ruotolo, K. J. Gillig, D. H. Russell, K. Fuhrer, M. Gonin, T. Egan and J. A. Schultz, J. Amer. Soc. Mass Spectr. 2002, 13, (166–169).
11. J. Huang, L. Wang, L. Chiang, J. Shiea, *J. Fullerene Sci. Technol.* 7, 541 (1999).
12. J. Shiea, J. Huang, C. Teng, J. Jeng, L. Wang, L. Chiang, *Anal. Chem.* 75, 3587 (2003).
13. J. Hybl, G. Lithgow, S. G. Buckley, *Appl. Spectrosc.* 57, 1207(2003).

What is claimed is:

1. A method of preparing an aerosolized sample for analysis by laser desorption mass spectrometry, comprising the steps of:

combining the sample with a matrix comprising a native or derivatized fullerene; and, producing aerosol particles from the combined sample and matrix.

2. The method of claim 1, wherein the native or derivatized fullerene is selected from the group consisting of $C_{60}$, $C_{70}$, $C_{76}$, $C_{84}$, and combinations thereof.

3. The method of claim 1, wherein the sample comprises peptides or proteins, or combinations thereof.

4. The method of claim 3, wherein the peptides or protein may be antibodies, enzymes or combinations thereof.

5. The method of claim 1, wherein the sample comprises a nucleic acid, a nucleic acid base, a nucleotide, a nucleoside, or combinations thereof.

6. The method of claim 1, wherein the sample comprises lipids, lipoproteins, or combinations thereof.

7. The method of claim 1, wherein the sample comprises phospholipids, ceramides, derivatives thereof, or combinations thereof.

8. The method of claim 1, wherein the sample comprises glycosylated proteins, glycosylated lipids, lipopolysaccharides, glycans, or combinations thereof.

9. The method of claim 1, wherein the sample comprises natural or synthetic organic polymers, natural or synthetic inorganic polymers, or combinations thereof.

10. The method of claim 1, wherein the sample comprises small organic molecules, organometallic molecules, or combinations thereof.

11. A method of preparing an aerosolized sample for analysis by laser desorption mass spectrometry, comprising the steps of:

combining the sample with a matrix comprising a native or derivatized nanotube; and, producing aerosol particles from the combined sample and matrix.

12. The method of claim 11, wherein the nanotube is a derivatized nanotube.

13. The method of claim 11, wherein the native or derivatized nanotube is a native or derivatized single wall nanotube.

14. The method of claim 11, wherein the sample comprises peptides, proteins, antibodies, enzymes, or combinations thereof.

15. The method of claim 11, wherein the sample comprises a nucleic acid, a nucleic acid base, a nucleotide, a nucleoside, or combinations thereof.

16. The method of claim 11, wherein the sample comprises a lipoprotein.

17. The method of claim 11, wherein the sample comprises phospholipids, ceramides, derivatives thereof, or combinations thereof.

18. The method of claim 11, wherein the sample comprises glycosylated proteins, glycosylated lipids, lipopolysaccharides, glycans, or combinations thereof.

19. The method of claim 11, wherein the sample comprises natural or synthetic organic polymers, natural or synthetic inorganic polymers, or combinations thereof.

20. The method of claim 11, wherein the sample comprises small organic molecules, organometallic molecules, or combinations thereof.

21. A method of preparing an aerosolized sample for analysis by laser desorption mass spectrometry, comprising the steps of:

combining the sample with a matrix comprising a surface derivatized inorganic particle; and, producing aerosol particles from the combined sample and matrix.

22. The method of claim 21, wherein the surface derivatized inorganic particle used as said matrix is selected from the group consisting of titanium nitride, aluminum nitride, boron nitride, carbonitride, carbon boron nitride, gold, molybdenum, copper, copper lithium alloy, platinum, silver, and combinations thereof.

23. A method of preparing an aerosolized sample for analysis by laser desorption mass spectrometry, comprising the steps of:

combining the sample with a matrix comprising nanoparticulates; and, producing aerosol particles from the combined sample and matrix.

24. A method for the analysis of samples using ion mobility resolved mass spectrometric data comprising the steps of:

introducing a sample comprising a liquid droplet or aerosol into a desorption source;

ionizing and desorbing gaseous analyte species from said liquid droplet or aerosol;

separating said analyte species from one another in an ion mobility cell; and, resolving said analyte species in an orthogonal time-of-flight mass spectrometer.

25. The method of claim 24, further comprising the step of forming said liquid droplet or aerosol with a vibrating orifice aerosol generator.

26. The method of claim 25, wherein said vibrating orifice aerosol generator generates droplets at the rate of up to 10 MHz.

27. The method of claim 24, wherein said step of ionizing and desorbing comprises ionizing and desorbing with coaxial laser irradiation.

28. The method of claim 24, wherein said sample is an aerosolized sample of a previously airborne pathogen.

29. The method of claim 28, wherein said pathogen is a bacteria, virus, prion, or cell.

30. The method of claim 24, wherein said sample is an aerosolized sample from a distribution of whole cells or whole cell lysate.

31. The method of claim 24 further comprising the step of correlating said ion mobility resolved mass spectrometric data with fluorescence data.

32. The method of claim 24, wherein said step of ionizing and desorbing comprises multiply impinging said sample with an energy source.

33. The method of claim 32, wherein said energy source is selected from the group consisting of a laser, a pulsed X-ray source, a chopped continuous infrared source, and a pulsed electron beam source.

34. An instrument for the collection of ion mobility resolved mass spectrometric data comprising:

an aerosol formation apparatus to form an aerosol;

a desorption ionization source coupled to said apparatus and capable of desorbing and ionizing species comprising the aerosol;

two ion mobility cells fluidly coupled to said aerosol formation apparatus, each mobility cell comprising a drift tube having a separation axis configured 180° to the separation axis of the drift tube of the other mobility cell; and, at least one time-of-flight mass spectrometer fluidly coupled to said mobility cell and having a flight tube orthogonal to the axis of the drift tube of the mobility cell.

35. The instrument of claim 34, wherein one of the mobility cells operates in positive mode and the other mobility cell operates in negative mode.

36. The instrument of claim 34, wherein the desorption ionization source comprises a laser.

37. The instrument of claim 36, wherein said laser emits a radiation beam which is coaxial to the path of a particle or droplet of said aerosol.

38. The instrument of claim 36, wherein said laser emits a radiation beam which is coaxial to a particle or droplet train of said aerosol.

39. The instrument of claim 36, wherein said aerosol comprises a sample in a fullerene-based matrix.

40. The instrument of claim 36, wherein said aerosol comprises a sample in a nanotube-based matrix.

41. The instrument of claim 40, wherein the nanotubes are single wall nanotubes.

42. The instrument of claim 34, wherein aerosolized matrix particles formed from said aerosol are fluidly coupled to said mobility cell using a single particle injection apparatus.

43. The instrument of claim 42, wherein said single particle injection apparatus is a converging nozzle aerosol interface.

44. The instrument of claim 43, further comprising a differentially pumped vacuum stage.

45. The instrument of claim 34, wherein said aerosol formation apparatus is a vibrating orifice aerosol generator.

46. The instrument of claim 45, wherein said vibrating orifice aerosol generator couples said mobility cells and said time-of-flight mass spectrometer to a liquid chromatograph.

47. The instrument of claim 45, wherein said vibrating orifice aerosol generator is directly interfaced to said mobility cell.

48. The instrument of claim 45, wherein the desorption ionization source comprises a laser.

49. The instrument of claim 48, wherein said laser emits a radiation beam which is coaxial to the path of a particle or droplet train of said aerosol.

50. The instrument of claim 48, wherein said laser emits a radiation beam which is coaxial to a particle or droplet train of said aerosol.

51. The instrument of claim 45, wherein said mobility cell further comprises multiapertures and periodic focusing fields.

52. The instrument of claim 34, further comprising a pathogen detection device which correlates the ion mobility resolved mass spectrometric data with fluorescence data.

53. The instrument of claim 34, further comprising a heated substrate fluidly coupled to or located within at least one of said ion mobility cells.

54. The instrument of claim 53, wherein said heated substrate comprises molybdenum or tantalum.

55. An apparatus for generating matrix particles for implantation into a sample for desorption/ionization comprising:

a nanoparticle source;

a charging device fluidly coupled to and receiving nanoparticles from said nanoparticle source and forming charged nanoparticles;

a focusing lens fluidly coupled to the charging device to focus said charged nanoparticles, a particle accelerator fluidly coupled to said focusing lens; and, a sample stage to position a sample and receive charged nanoparticles from said particle accelerator.

* * * * *